United States Patent [19]
Yanagisawa

[11] Patent Number: 5,688,640
[45] Date of Patent: Nov. 18, 1997

[54] METHODS OF SCREENING OF EFFECTORS OF ENDOTHELIN CONVERTING ENZYME-1

[75] Inventor: Masashi Yanagisawa, Dallas, Tex.

[73] Assignee: Board of Regents, The University of Texas System, Austin, Tex.

[21] Appl. No.: 289,112

[22] Filed: Aug. 10, 1994

[51] Int. Cl.$^6$ ............................ C12N 15/63; C12Q 1/68
[52] U.S. Cl. ........................... 435/6; 435/24; 435/29; 435/69.1; 435/172.3; 435/252.3
[58] Field of Search .................. 435/6, 29, 69.1, 435/172.3, 252.3, 24

[56] References Cited

U.S. PATENT DOCUMENTS

| | | | |
|---|---|---|---|
| 5,231,166 | 7/1993 | Masaki et al. | 530/324 |
| 5,294,569 | 3/1994 | Masaki et al. | 536/23.5 |
| 5,338,726 | 8/1994 | Shiosaki et al. | 514/17 |
| 5,384,243 | 1/1995 | Gutkind et al. | 435/6 |
| 5,427,922 | 6/1995 | Fujisawa et al. | 435/69.1 |

OTHER PUBLICATIONS

Arai et al., Bioxi. Biotech. Biochem. 57(11) 1944–1945, 1993.

Shimada et al. Journal of Biological Chemistry 269(28):18275–18278, Jul. 15, 1994.

Ikura et al. Biochemical and Biophysical Research Communications 203(3):1417–1422, Sep. 30, 1994.

Ahn, K., Beningo, K., Olds, G., and Hupe, D. (1992). The endothelin–converting enzyme from human umbilical vein is a membrane–bound metalloprotease similar to that from bovine aortic endothelial cells. *Proc. Natl. Acad. Sci. USA* 89:8606–8610.

Clozel, M., Breu, V., Burri, K., Cassal, J.-M., Fischli, W., Gray, G.A., Hirth, G., Loffler, B.-M., Muller, M., Neldhart, W., and Ramuz, H. (1993). Pathophysiological role of endothelin revealed by the first orally active endothelin receptor antagonist. *Nature* 365:759–761.

Inoue, A., Yanagisawa, M., Takuwa, Y., Mitsui, Y., Kobayashi, M., and Masaki, T. (1989b). The human preproendothelin–1 gene. Complete nucleotide sequence and regulation of expression. *J. Biol. Chem.* 264:14954–14959.

McMahon, E.G., Palomo, M.A., Moore, W.M., McDonald, J.R., and Stern, M.K. (1991). Phosphoramidon blocks the pressor activity of porcine big endothelin–1–(1–39) in vivo and conversion of big endothelin–1–(1–39) to endothelin–1–(1–21) in vitro. *Proc. Natl. Acad. Sci. USA* 88:703–707.

Nishikori, K., Akiyama, H., Inagaki, Y., Ohta, H., Kashiwabara, T., Iwamatsu, A., Nomizu, M., and Morita, A. (1991). Receptor binding affinity and biological activity of c–terminal elongated forms of endothelin–1. *Neurochem. Int.* 18:535–539.

(List continued on next page.)

*Primary Examiner*—W. Gary Jones
*Assistant Examiner*—Paul B. Tran
*Attorney, Agent, or Firm*—Arnold, White & Durkee

[57] ABSTRACT

Endothelin-1 (ET-1), a 21-residue vasoactive peptide, is produced in vascular endothelial cells from the 38-residue inactive intermediate, big endothelin-1 via a specific cleavage at Trp21-Val22. The protease that catalyzes the conversion, endothelin converting enzyme (ECE), constitutes a potential regulatory site for the production of the active peptide. Disclosed herein is the identification of ECE-1, a novel membrane-bound neutral $Zn^{2+}$ metalloprotease that is expressed abundantly in endothelial cells in vivo, and structurally related to neutral endopeptidase 24.11 and Kell blood group protein. When transfected into cultured cells that normally secrete only big ET-1, the ECE-1 cDNA conferred the ability to secrete mature ET-1. In transfected cells, ECE-1 processes endogenously synthesized big ET-1 as well as exogenously supplied big ET-1, which interacts with ECE-1 on the cell surface. The remarkable specificity of ECE-1 provides a target for selective pharmacological intervention to alter ET-1 production in certain clinical disorders.

6 Claims, 22 Drawing Sheets

OTHER PUBLICATIONS

Ohnaka, K., Takayanagi, R., Nishikawa, M., Haji, M., and Nawata, H. (1993). Purification and characterization of a phosphoramidon–sensitive endothelin–converting enzyme in porcine aortic endothelium. *J. Biol. Chem.* 268:26759–26766.

Okada, K., Miyazaki, Y., Takada, J., Matsuyama, K., Yamaki, T., and Yano, M. (1990). Conversion of big endothelin–1 by membrane–bound metalloendopeptidase in cultured bovine endothelial cells. *Biochem. Biophys. Res. Comm.* 171:1192–1198.

Opgenorth, T.J., Wu–Wong, J.R., and Shiosaki, K. (1992). Endothelin–converting enzymes. *FASEB J.* 6:2653–2659.

Sawamura, T., Kasuya, Y., Matshushita, Y., Suzuki, N., Shinmi, O., Kishi, N., Sugita, Y., Yanagisawa, M., Goto, K., Masaki, T., and Kimura, S. (1991). Phosphoramidon inhibits the intracellular conversion of big endothelin–1 to endothelin–1 in cultured endothelial cells. *Biochem. Biophys. Res. Comm.* 174:779–784.

Seidah, N.G., Day, R., Marcinkiewicz, M., and Chretien, M. (1993). Mammalian paired basic amino acid convertases of prohormones and proproteins. *Ann. New York Acad. Sci.* 680:135–146.

Takahashi, M., Matsushita, Y., Iijima, Y., and Tanzawa, K. (1993). Purification and characterization of endothelin–converting enzyme from rat lung. *J. Biol. Chem.* 268:21395–21398.

Turner, A.J. (1993). Endothelin–converting enzymes and other families of metalloendopeptidases. *Biochem. Soc. Trans.* 21:596–701.

Vijayaraghavan, J., Scicli, A.G., Carretero, O.A., Slaughter, C., Moomaw, C., and Hersh, L.B. (1990). The hydrolysis of endothelins by neutral endopeptidase 24.11 (enkephalinase). *J. Biol. Chem.* 265:14150–14155.

Waxman, L., Doshi, K.P., Gaul, S.L., Wang, S., Rodney, A.B., and Stern, A.M. (1993). Identification and characterization of endothelin converting activity from EAHY 926 cells: Evidence for the physiologically relevant human enzymes. *Arch. Biochem. Biophy.* 308:240–253.

Yanagisawa, M. (1994). The endothelin system: A new target for therapeutic intervention. *Circulation* 89:1320–1322.

Yanagisawa, M., Kurihara, H., Kimura, S., Tomobe, Y., Kobayashi, M., Mitsui, Y., Yazaki, Y., Goto, K., and Masaki, T. (1988). A novel potent vasoconstrictor peptide produced by vascular endothelial cells. *Nature* 332:411–415.

Inoue, A., Masashi, Y., Sadao, K., Yoshitoshi, K., Takashi, M., Tatsutoshi, G., and Tomoh, M.. The human endothelin family: Three structurally and pharmacologically distinct isopeptides predicted by three separate genes. *Proc. Natl. Acad. Sci. USA*, 86:2863–2867 (1989).

```
AGCGCGGCTGGGCTGGGCTGCTTGACTCCGAGCTG        35

CTGAGCAGGGTGGCCGTTCCTCTCCTGGATTAGGA        70

CGGTTCCGTGGGAACCAGACCACCCCTGAGACGGG       105
                        ***
AGGGCGGCCCTGATGTCTCCCCGGGGCCAGGAT         138
              MetSerProArgGlyGlnAsp         7

CTGCTGCGGAGCCCCCTCCTCCTGGGCAGCGAG         171
LeuLeuArgSerProLeuLeuLeuGlySerGlu          18

GCCCCTGGGCTCACGTCCTCCCCGTTCCGCCTG         204
AlaProGlyLeuThrSerSerProPheArgLeu          29

CCTCCTTCCCTGCAGGTGAACTTCCGAGGCCCC         237
ProProSerLeuGlnValAsnPheArgGlyPro          40

CGGAACGGCCAGAGATGCTGGGCCGCCAGGACC         270
ArgAsnGlyGlnArgCysTrpAlaAlaArgThr          51

CCGGTGGAGAAGCGGCTGGTGGTGCTGGTGGCG         303
ProValGluLysArgLeuValValLeuValAla          62
```

FIG. 1A

```
CTCCTGGCGGCGGCATTGGTGGCTGTTTGGCA              336
LeuLeuAlaAlaAlaLeuValAlaCysLeuAla              73

GTACTGGGCATCCAATACCAGACAAGAACGCCC             369
ValLeuGlyIleGlnTyrGlnThrArgThrPro              84

TCGGTGTGCCTAAGTGAGGGCTGCATCTCGGTG             402
SerValCysLeuSerGluGlyCysIleSerVal              95

ACCAGCTCCATCTTGAGTTCCATGGACCCCACG             435
ThrSerSerIleLeuSerSerMetAspProThr             106

GTGGACCCCTGCCAGGACTTCTTCACCTATGCC             468
ValAspProCysGlnAspPhePheThrTyrAla             117

TGTGGCGGCTGGATCAAAGCCAACCCCGTGCCG             501
CysGlyGlyTrpIleLysAlaAsnProValPro             128

GATGGCCACTCGCGCTGGGGGACCTTCAGCAAC             534
AspGlyHisSerArgTrpGlyThrPheSerAsn             139

CTCTGGGAACACAACCAAGCCATCATCAAGCAC             567
LeuTrpGluHisAsnGlnAlaIleIleLysHis             150
```

FIG. 1B

```
CTCCTTGAAAACTCCACGGCCAGCGTGAGCGAG              600
LeuLeuGluAsnSerThrAlaSerValSerGlu              161
                ‡
GCAGAGAGGAAGGCCCAGGTGTACTACCGAGCC              633
AlaGluArgLysAlaGlnValTyrTyrArgAla              172

TGCATGAACGAAACCAGGATTGAGGAGCTCAAG              666
CysMetAsnGluThrArgIleGluGluLeuLys              183
         ‡
GCCAAACCCCTGATGGAGCTCATTGAGAAGCTC              699
AlaLysProLeuMetGluLeuIleGluLysLeu              194

GGCGGCTGGAACATCACGGGGCCCTGGGACAAG              732
GlyGlyTrpAsnIleThrGlyProTrpAspLys              205
                ‡
GACAACTTCCAGGACACCCTGCAGGTGGTCACA              765
AspAsnPheGlnAspThrLeuGlnValValThr              216

TCCCACTACCACACCTCCCCCTTCTTCTCCGTC              798
SerHisTyrHisThrSerProPhePheSerVal              227

TACGTCAGTGCCGACTCCAAGAATTCCAACAGC              831
TyrValSerAlaAspSerLysAsnSerAsnSer              238
```

FIG. 1C

| | |
|---|---:|
| AACGTGATCCAAGTGGACCAGTCTGGCCTGGGC | 864 |
| AsnValIleGlnValAspGlnSerGlyLeuGly | 249 |
| | |
| TTACCCTCAAGAGATTATTACCTGAACAAAACC | 897 |
| LeuProSerArgAspTyrTyrLeuAsnLysThr | 260 |
| ‡ | |
| GAGAATGAGAAGGTGCTGACGGGATACCTGAAC | 930 |
| GluAsnGluLysValLeuThrGlyTyrLeuAsn | 271 |
| | |
| TACATGGTCCAGCTGGGGAAGCTGCTGGGAGGA | 963 |
| TyrMetValGlnLeuGlyLysLeuLeuGlyGly | 282 |
| | |
| GGGGCCGAGGACACCATCCGGCCCCAGATGCAG | 996 |
| GlyAlaGluAspThrIleArgProGlnMetGln | 293 |
| | |
| CAGATCCTGGACTTTGAGACGGCGCTGGCCAAC | 1029 |
| GlnIleLeuAspPheGluThrAlaLeuAlaAsn | 304 |
| ‡ | |
| ATCACCATCCCCCAGGAGAAGCGCCGGGACGAG | 1062 |
| IleThrIleProGlnGluLysArgArgAspGlu | 315 |
| | |
| GAACTCATCTACCACAAAGTGACGGCGGCTGAG | 1095 |
| GluLeuIleTyrHisLysValThrAlaAlaGlu | 326 |

FIG. 1D

```
TTGCAGACCTTGGCGCCGCCATCAACTGGCTG              1128
LeuGlnThrLeuAlaProAlaIleAsnTrpLeu              337

CCCTTCCTCAACACCATCTTCTACCCCGTGGAG              1161
ProPheLeuAsnThrIlePheTyrProValGlu              348

ATCAATGAATCAGAGCCTATTGTCATCTACGAC              1194
IleAsnGluSerGluProIleValIleTyrAsp              359
    ǂ
AAAGAATACCTGAGCAAGGTCTCCACCCTCATC              1227
LysGluTyrLeuSerLysValSerThrLeuIle              370

AACAGCACAGACAAATGCCTGCTGAACAACTAC              1260
AsnSerThrAspLysCysLeuLeuAsnAsnTyr              381
  ǂ
ATGATCTGGAACCTGGTACGGAAGACGAGCTCC              1293
MetIleTrpAsnLeuValArgLysThrSerSer              392

TTCCTCGATCAGCGCTTCCAGGACGCCGACGAG              1326
PheLeuAspGlnArgPheGlnAspAlaAspGlu              403

AAGTTCATGGAAGTCATGTATGGGACCAAGAAG              1359
LysPheMetGluValMetTyrGlyThrLysLys              414
```

FIG. 1E

| | |
|---|---|
| ACGTGTCTTCCCCGCTGGAAGTTTTGTGTGAGT | 1392 |
| ThrCysLeuProArgTrpLysPheCysValSer | 425 |
| | |
| GATACAGAGAACACCTTGGGCTTCGCCCTGGGC | 1425 |
| AspThrGluAsnThrLeuGlyPheAlaLeuGly | 436 |
| | |
| CCCATGTTCGTCAAAGCGACCTTCGCTGAGGAC | 1458 |
| ProMetPheValLysAlaThrPheAlaGluAsp | 447 |
| | |
| AGCAAGAACATAGCCAGCGAGATCATCCTGGAG | 1491 |
| SerLysAsnIleAlaSerGluIleIleLeuGlu | 458 |
| | |
| ATCAAGAAGGCGTTTGAAGAGAGCCTGAGCACC | 1524 |
| IleLysLysAlaPheGluGluSerLeuSerThr | 469 |
| | |
| CTGAAGTGGATGGATGAAGATACTCGGAAATCG | 1557 |
| LeuLysTrpMetAspGluAspThrArgLysSer | 480 |
| | |
| GCCAAGGAAAAGGCGGACGCGATCTACAACATG | 1590 |
| AlaLysGluLysAlaAspAlaIleTyrAsnMet | 491 |
| | |
| ATAGGCTACCCCAACTTTATCATGGACCCCAAG | 1623 |
| IleGlyTyrProAsnPheIleMetAspProLys | 502 |

FIG. 1F

| | |
|---|---|
| GAGCTGGACAAAGTGTTCAATGACTACACCGCT | 1656 |
| GluLeuAspLysValPheAsnAspTyrThrAla | 513 |
| GTGCCAGACCTCTACTTCGAGAACGCCATGCGG | 1689 |
| ValProAspLeuTyrPheGluAsnAlaMetArg | 524 |
| TTTTTCAACTTCTCCTGGAGGGTCACTGCCGAC | 1722 |
| PhePheAsnPheSerTrpArgValThrAlaAsp | 535 |
| ǂ | |
| CAGCTCCGGAAAGCGCCCAACAGAGATCAGTGG | 1755 |
| GlnLeuArgLys<u>AlaProAsnArgAspGlnTrp</u> | 546 |
| AGCATGACCCCGCCCATGGTGAACGCCTACTAC | 1788 |
| <u>SerMetThrProProMetValAsnAlaTyrTyr</u> | 557 |
| TCGCCCACCAAGAACGAGATCGTGTTTCCGGCC | 1821 |
| <u>SerProThrLysAsnGluIleValPheProAla</u> | 568 |
| ●●●●●●●●●●●●●●● | |
| GGAATCCTGCAGGCGCCATTCTACACCCGCTCT | 1854 |
| <u>GlyIleLeuGlnAlaProPheTyrThrArgSer</u> | 579 |
| TCACCCAATGCCTTAAACTTCGGCGGCATCGGC | 1887 |
| <u>SerProAsnAlaLeuAsnPheGlyGlyIleGly</u> | 590 |
| ●●●●●●●●●●●●●●●●● | |

FIG. 1G

```
GTCGTCGTGGGCCACGAGCTGACTCATGCTTTT              1920
ValValValGlyHisGluLeuThrHisAlaPhe               601

GATGATCAAGGCCGAGAGTACGACAAGGATGGG              1953
AspAspGlnGlyArgGluTyrAspLysAspGly               612

AACCTCCGGCCCTGGTGGAAGAACTCGTCCGTG              1986
AsnLeuArgProTrpTrpLysAsnSerSerVal               623
                  ‡
GAGGCGTTCAAGCAGCAGACCGCGTGCATGGTG              2019
GluAlaPheLysGlnGlnThrAlaCysMetVal               634

GAGCAGTACGGCAACTATAGCGTGAACGGGGAG              2052
GluGlnTyrGlyAsnTyrSerValAsnGlyGlu               645
                  ‡
CCGGTGAACGGCCGGCACACCCTCGGCGAAAAC              2085
ProValAsnGlyArgHisThrLeuGlyGluAsn               656

ATCGCCGACAACGGGGGCCTCAAGGCGGCCTAT              2118
IleAlaAspAsnGlyGlyLeuLysAlaAlaTyr               667

CGGGCCTACCAGAACTGGGTCAAGAAGAATGGG              2151
ArgAlaTyrGlnAsnTrpValLysLysAsnGly               678
```

FIG. 1H

```
GCTGAGCAGACACTGCCCACCCTGGGTCTCACC        2184
AlaGluGlnThrLeuProThrLeuGlyLeuThr         689

AACAACCAGCTCTTCTTCCTGAGTTTTGGACAG        2217
AsnAsnGlnLeuPhePheLeuSerPheGlyGln         700

GTCTGGTGTTCCGTCCGCACCCCGAGAGTTCG         2250
ValTrpCysSerValArgThrProGluSerSer         711

CACGAAGGTCTCATCACCGATCCCACAGCCCC         2283
HisGluGlyLeuIleThrAspProHisSerPro         722

TCCCGCTTCCGGGTCATCGGCTCCATCTCCAAC        2316
SerArgPheArgValIleGlySerIleSerAsn         733

TCCAAGGAGTTCTCGGAACACTTCCACTGCCCG        2349
SerLysGluPheSerGluHisPheHisCysPro         744

CCCGGCTCACCCATGAACCCGCATCACAAGTGT        2382
ProGlySerProMetAsnProHisHisLysCys         755

GAAGTCTGGTGAAGGGCCAGGCACCCAGAGCCG        2415
GluValTrp***                              758
```

FIG. 1I

```
AGATGGAGGGCAAGGCGGGGGGAGGCCTGAGAACA    2450

CCCCCCTGGGCCCACAAGACTGCCCCTCCATCCG     2485

GCGGCCAGCCCCTCCCCGACGCTGCAGGGTGGT      2520

CAGCCGGAACCAAGCCTGTGACATGAGCTCTACC     2555

GTAAGCTGAGATTTGACCCCTGTGAAGACCCGCT     2590

CATCCCAGGCACACGTGTGTCAACTCTGATGGGTG    2625

TTGGGGCGTTAGCCGGGTTGCCCACCGGGCCTGGA    2660

CCCTCACCGACAAGGGCAGGGGAGCCCAGCCCCCT    2695

CCGCCCACATGCAGCACCAGATATACCACAAATAC    2730

CACTGTGTCAAATGCTTTAAAGATATATTTTTGGG    2765

GAAACTATTTTTTAAACATAGTGGAATACACTGGA    2800

AACCTTCAGGGAAATGATGCATTTAAAACACTTTT    2835
```

FIG. 1J

TTTTTTATGGAAAGGATCGGTATATTTATTATGTT    2870
         ↑poly (A)
CTGTTTTTCTAAATAACCT--1.5 kb--TCCGTGCGACTG

TAGTTCTGTGTGGCACCATTGTAACTGAAATAAAGTACTNA

TACCGAT - poly (A)

FIG. 1K

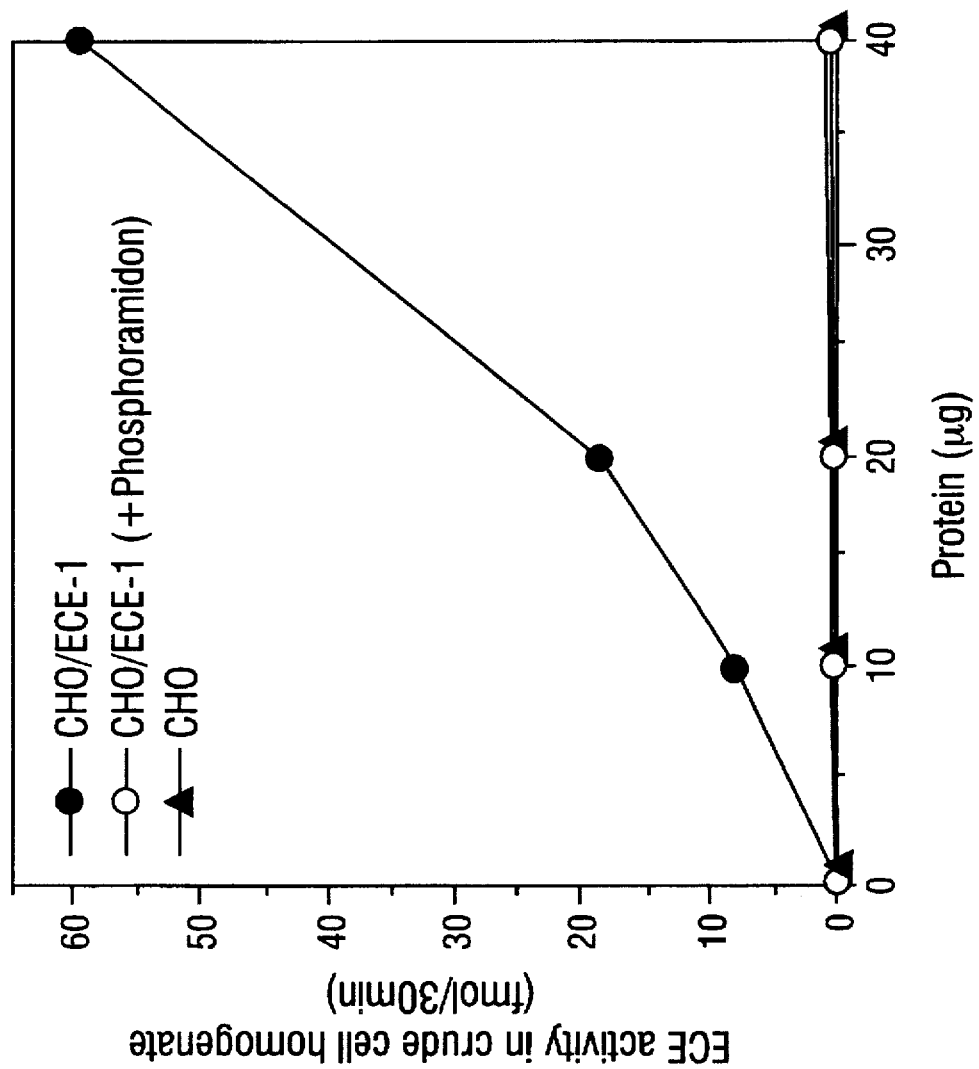

METHODS OF SCREENING OF EFFECTORS OF ENDOTHELIN CONVERTING ENZYME-1

BACKGROUND OF THE INVENTION

1. Field of the Invention

The present invention relates generally to the field of vascular homeostasis, the control of vasodilation by peptide regulators and their role in diseases such as high blood pressure, kidney disease and certain types of strokes. More particularly, the invention relates to the field of proteases that activate the peptide regulators and to the family of membrane bound metalloproteases.

2. Description of the Related Art

Local interactions between vascular endothelium and underlining smooth muscle exemplify the importance of paracrine cellular communications in vascular homeostasis. Endothelial cells regulate the function of smooth muscle cells by producing an array of vasoactive molecules such as nitric oxide and endothelin-1 (ET-1) in response to various stimuli (Vane and Botting, 1992). The release of these factors causes acute and/or chronic changes in local vascular tone leading to alterations in local blood flow, and, in the long term, changes in smooth muscle proliferation, migration and remodelling. ET-1, the first member of the endothelin peptide family, is the most potent vasoconstrictor substance known (Yanagisawa, 1994; Yanagisawa et al., 1988).

Three known endothelins, ET-1, ET-2, and ET-3, are produced by a variety of mammalian cell types, including epithelial, interstitial and neuronal cells, with distinct but partially overlapping tissue distributions. Vascular endothelium is the most abundant source of ET-1 in vivo, and ET-1 is the only isopeptide produced by endothelial cells. The production of ET-1 is tightly regulated at the level of mRNA transcription (Lee et al., 1991a). In vascular endothelial cells, the peptide, once synthesized, is secreted via the constitutive pathway without further regulation at the level of exocytosis. Endothelins act on two pharmacologically distinct subtypes of G protein-coupled receptors termed $ET_A$ and $ET_B$ (Arai et al., 1990; Sakurai et al., 1990), that are expressed on a wide variety of vascular and non-vascular target cells, eliciting, for example, contraction and proliferation of vascular smooth muscle cells and release of nitric oxide from endothelial cells (Simonson and Dunn, 1991).

Derangements in the highly regulated production of such powerful vasoactive molecules can lead to serious pathology. Recent studies with highly specific endothelin receptor antagonists have demonstrated important roles for ET-1 in a number of models of various diseases, including ischemic and cyclosporine-induced renal failure (Bloom et al., 1993; Gellai et al., 1994; Kivlighn et al., 1993), progressive proliferative glomerulonephropathy (Benigni et al., 1993), cerebrovascular spasm (Clozel et al., 1993; Ito et al., 1993), acute myocardial infarction (Grover et al., 1993), ischemic neuronal damage (Ohlstein et al., 1994), post-denudation intimal hyperplasia/restenosis (Ohlstein et al., 1994), and systemic and pulmonary hypertension (Clozel et al., 1993; Giaid et al., 1993, Nishikibe et al., 1993; Ohlstein et al., 1994; Yokokawa et al., 1991).

Furthermore, a recent report of ET-1 gene targeting in mice (Kurihara et al., 1994) showed that mice homozygous for ET-1 null mutation manifest severe hypoplasia of the craniofacial tissues derived from the first branchial arch, indicating the importance of ET-1 in the normal development of neural crest-derived tissues. Mice heterozygous for the ET-1 null mutation had reduced plasma and tissue levels of ET-1, but they exhibited a paradoxical increase in blood pressure. These results indicate the existence of a complex ET-1 mediated mechanism for basal blood pressure regulation that may involve actions of ET-1 in the central nervous system as well as in peripheral tissues.

The three endothelin isopeptides are each produced from corresponding ≈200-residue prepropolypeptides that are encoded by separate genes (Inoue et al., 1989a). Longer intermediates termed big ET-1, -2 and -3 (38–41 amino acids) are first excised from the (pre-) propeptides by proteases that cleave at sites that contain paired basic amino acids (Seidah et al., 1993). Big endothelins, which are biologically inactive, are then further cleaved at Trp21-Val/Ile22 to produce the 21-residue mature peptides. The importance of precise clipping is illustrated by the finding that the vasoconstrictor activity of ET-1(1-20) and ET-1(1-22) is at least three orders of magnitude weaker than authentic ET-1 (1-21) (Nishikori et al., 1991). Simple C-terminal amidation of Trp21 also causes a marked decrease in the biological activities of the peptide (Nakajima et al., 1989).

The putative endopeptidase(s) that catalyzes the highly specific cleavage at Trp21 has been termed endothelin converting enzyme (ECE) (Opgenorth et al., 1992; Yanagisawa et al., 1988). Two distinct lines of evidence have indicated that ECE is inhibited by the metalloprotease inhibitor phosphoramidon. First, exogenously administered big ET-1 is converted, albeit inefficiently, into mature ET-1 both in whole animals and in isolated perfused organs. Phosphoramidon consistently inhibits the conversion in most assay systems (McMahon et al., 1991; Opgenorth et al., 1992). Second, cultured endothelial cells secrete mature and big ET-1 in the ratio of 2-5:1, indicating an efficient (>60–80%) conversion of the endogenously produced big ET-1. Phosphoramidon added to the medium decreases the production of mature ET-1 in a dose dependent manner, causing a concomitant increase in the amount of big ET-1 (Sawamura et al., 1991). Whether big ET-1 is cleaved intracellularly or extracellularly is unknown, although the rapid conversion of exogenously applied big ET-1 is consistent with cell surface conversion. It is also unclear as to whether the same ECE molecule is responsible for the conversion of both endogenous and exogenous big ET-1.

Endothelial cells possess membrane-bound ECE activities. A number of studies with crude membranes (Ahn et al., 1992; Okada et al., 1990) and purified enzyme preparations (Ohnaka et al., 1993; Takahashi et al., 1993; Waxman et al., 1993) have shown that the endothelial ECE activity is that of a neutral metalloprotease, and that the enzyme seems to be a glycoprotein with an apparent molecular mass of 120–130 kD under reduced conditions. This ECE activity is inhibited by relatively high concentrations of phosphoramidon in the low μM range, but not by thiorphan, a more specific inhibitor of neutral endopeptidase 24.11 (NEP) (Roques et al., 1993), or by captopril, a specific angiotensin converting enzyme inhibitor. These pharmacological profiles suggest that ECE is a novel metalloprotease. Unfortunately, it has been difficult to relate these ECE activities assayed in the test tube to the physiologically relevant ECE activities that function in vivo. In addition it has not been possible to overproduce ECE in order to determine the molecular mechanisms of vasoconstriction and to design new inhibitory agents to be used as therapeutic agents.

SUMMARY OF THE INVENTION

The present invention seeks to overcome these and other drawbacks inherent in the prior art by identifying ECE-1, a novel membrane-bound metalloprotease, providing evidence for the physiological relevance of ECE-1 both in the secretion of mature ET-1 from cells expressing preproET-1 as well as in the conversion of exogenous big ET-1 on the cell surface, and by providing the isolation of a mammalian endothelin converting enzyme-1 gene. With the use of the present invention, high levels of ECE-1 activity can be expressed in transfected tissue culture cells or in prokaryotic cells. In addition, cell lines which permanently express high levels of ECE-1 can be readily generated and used.

In certain embodiments the present invention is an isolated segment of DNA and particularly a segment of DNA which encodes an endothelin converting enzyme polypeptide comprising an amino acid sequence in accordance with the amino acid sequence as set forth herein as SEQ ID NO:2. This DNA segment may also be defined as comprising the nucleic acid sequence as set forth herein as SEQ ID NO:1 or SEQ ID NO:3. It is understood that in addition to the DNA sequences disclosed herein in FIG. 1A, the complement of the disclosed sequences, the RNA sequence encoded by the DNA segment and the complement of the RNA sequence are also encompassed by the present claimed invention. The complement of a DNA or RNA sequence is well known in the art and is based on the Watson-Crick pairing of nucleic acid polymers. The complement of a nucleic acid segment is generated by converting all "G" residues to "C" residues, all "C" residues to "G" residues, all "A" residues to "T" (in the case of DNA) or "U" (in the case of RNA) and all "T" or "U" residues to "A", and then reversing the 5' to 3' orientation of the generated sequence. As used herein therefore, the term "complement" defines a second strand of nucleic acid which will hybridize to a first strand of nucleic acid to form a duplex molecule in which all base pairs are matched as G:C, C:G, A:T/U or T/U:A.

The present invention may also be described in certain embodiments as a nucleic acid segment that is hybridizable to the DNA segment of SEQ ID NO:1 or SEQ ID NO:3 under stringent conditions. Hybridizable is understood to mean the formation of a double stranded molecule or a molecule with partial double stranded structure. Stringent conditions are those that allow hybridization between two nucleic acid sequences with some degree of homology, but precludes hybridization of random sequences. For example, hybridization at low temperature and/or high ionic strength is termed low stringency and hybridization at high temperature and/or low ionic strength is termed high stringency. Some examples of ranges that may be employed are for low stringency, from 0.15–0.9M NaCl at a temperature of 20°–50° C. might be employed, and for high stringency, from 0.02–0.15M NaCl at a temperature of 50°–70° C. might be employed. It is understood that the temperature and ionic strength of a desired stringency are applicable to particular probe lengths, to the length and base content of the sequences and to the presence of formamide or other solvents in the hybridization mixture and that these ranges are mentioned by way of example only.

It is understood in the art that a nucleic acid sequence will hybridize with a complementary nucleic acid sequence under high stringency conditions even though some mismatches may be present, particularly in complementary stretches of more than about 15-17 bases. Such closely matched, but not perfectly complementary sequences are also encompassed by the present invention. For example, differences may occur through genetic code degeneracy, or by naturally occurring or man made mutations and such mismatched sequences would still be encompassed by the present claimed invention. It is also understood that the DNA segment of the present invention may be defined as having the nucleic acid sequence of SEQ ID NO:1 or SEQ ID NO:3, meaning the sequences as disclosed herein in FIG. 6A.

It is also understood that the DNA segment of the present invention may be under the control of a promoter. The promoter may be the normal promoter which controls the expression of the DNA segment in its native tissue, or it may be a recombinant promoter. By recombinant promoter is meant a promoter derived from another source, either another within the same cell or from a different type of cell or even from a different organism. promoter sequence is then joined to the DNA segment in an upstream position (5') from the start of the gene. Preferred promoters are cytomegalovirus major immediate early gene promoter, simian virus 40 late gene promoter and Baculovirus *Autographa californica* nuclear polyhedrosis virus polyhedrin gene promoter. Alternatively, the promoter may be an inducible promoter such as the lactose operon promoter.

The DNA segment of the present invention may also comprise a vector capable of replicating within a cell. In particular, the DNA segment may comprise a recombinant vector. A large number of vectors are available commercially and are well known to those in the art. In general, a vector is compatible with a particular cell type such as prokaryotic, eukaryotic, yeast, plant, insect, etc. The matching of compatible vectors and host cells is well known and routinely practiced in the art. The vector may be further defined as comprising the nucleic acid sequence set forth in SEQ ID NO:1, or as a recombinant expression vector capable of expressing an endothelin converting enzyme polypeptide on introduction into a host cell, and the vector may be further defined as capable of expressing an endothelin receptor. A preferred vector in the practice of the present invention is the pME18Sf vector.

In certain embodiments, the vector which comprises the DNA segment of the present invention will be an expression vector. In this embodiment, the DNA segment encoding the endothelin converting enzyme will be transcribed into mRNA and the mRNA will be translated into a polypeptide. Thus, the recombinant cell will express the ECE polypeptide. The vector in this embodiment will comprise the signal sequences to express the gene in the particular cell type. For instance the promoter/enhancer regions, translational start sites and downstream signals such as the polyadenylation site if necessary, will be compatible with the host cell transcription/translational mechanisms.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bg II site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

As used herein, the term "engineered" or "recombinant" cell is intended to refer to a cell into which a recombinant gene, such as a gene encoding an endothelin converting enzyme has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e. they will not contain introns), a copy of a genomic gene, or will include genes positioned adjacent to a promoter not naturally associated with the particular introduced gene.

Preferred cell lines to be used in the present invention are eukaryotic cells and more preferred are mammalian cells and even more preferably CHO cells. The host cell may be further defined as comprising the DNA segment in accordance with SEQ ID NO:1, positioned in a recombinant vector, although it is understood that the DNA segment may also be integrated into the host genome, and in particular, the host cell may be defined as comprising a recombinant expression vector and expressing a endothelin converting enzyme. The host cell may further express the preproET-1 polypeptide. The gene for preproET-1 may be expressed from the same expression vector as the ECE or from a separate recombinant expression vector or even from the host genome.

It is understood that smaller nucleic acid segments which comprise as their nucleic acid sequence the nucleic acid sequence of SEQ ID NO:1 or SEQ ID NO:3 are also encompassed by the present invention. For example, nucleic acid segments comprising a segment of at least ten, fifteen, twenty, thirty, fifty or sixty contiguous nucleotides that correspond to SEQ ID NO:1 or SEQ ID NO:3 or their complements are also a part of the present invention. In addition, nucleic acid segments comprising a segment of at least one hundred, or one thousand, or even up to a 2,889 contiguous nucleotides that correspond to the nucleic acid sequence of SEQ ID NO:1 or SEQ ID NO:3 and including the nucleic acid sequence of SEQ ID NO:1 or its complement are also a part of and are included in the present claimed invention.

In certain embodiments of the present invention, the recombinant host cell which comprises a vector and expresses the ECE polypeptide may be further defined as comprising a nucleic acid fragment of up to 10,000, up to 5,000 or up to 3,000 basepairs in length. It may further be defined as comprising a nucleic acid fragment of up to 1,000, up to 500, up to 100 or even up to 50 basepairs in length. The vector may be an RNA molecule or more preferably a DNA molecule.

In certain alternate embodiments, the present invention is a polypeptide, a protein, or even a peptide, comprising as a part of its amino acid sequence the amino acid sequence as set forth in SEQ ID NO:2, or even a polypeptide or protein with the amino acid sequence of SEQ ID NO:2. It is also understood that amino acid fragments or peptides of the present invention will have utility, for example as antigenic epitopes, in the production of antibodies or as screening agents. Therefore, a peptide which comprises as a part of its amino acid sequence at least a four amino acid stretch, at least a ten amino acid stretch, at least a twenty amino acid stretch, at least a fifty amino acid stretch, at least a one hundred amino acid stretch, at least a two hundred amino acid stretch, at least a five hundred amino acid stretch or even up to a seven hundred fifty eight amino acid stretch corresponding to the amino acid sequence of SEQ ID NO:2 will be encompassed by the scope and the spirit of the appended claims.

An important use of the peptide fragments of the present invention is the production of antibodies which are immunoreactive with said peptides. These antibodies will have utility as diagnostic agents for the expression of ECE as well as use as possible inhibitors of ECE activity. Therefore antibodies which are produced with the peptides or polypeptides of the present invention, or those antibodies which are found to be immunoreactive with the peptides or polypeptides of the present invention are also a part of this invention. The antibodies may be polyclonal antibodies or monoclonal antibodies and may be derived from any source such as goat, mouse, bovine, equine, simian or any other source, even including recombinantly produced antibodies. The production of anti-idiotype antibodies is also well known in the art, and any such anti-idiotypic antibodies are also encompassed by the present invention.

An embodiment of the present invention is a method of producing endothelin. The method comprises contacting big endothelin with a composition consisting essentially of a partially purified endothelin converting enzyme. It is known that endothelin converting enzymes have some proteolytic activity for all three forms of big endothelin (endothelin 1, 2 and 3) and that all such activity is encompassed by the present claimed invention. The preferred method is a method of producing endothelin 1 by contacting big endothelin-1 with an endothelin converting enzyme-1. The most preferred enzyme is ECE-1 purified from bovine adrenal cortex.

An alternative method of the present invention is a method of producing endothelin-1 (ET-1) in a cell. This method comprises expressing recombinant endothelin converting enzyme in the cell and contacting the endothelin converting enzyme with big endothelin. This method may further comprise isolating the ET-1 produced in the cell. The big endothelin may be expressed in the same cell as the ECE, either from an expression vector, such as a recombinant expression vector, or even from the host genome. Expression from the host genome may be from the naturally occurring gene or may be a recombinantly introduced gene. It is also understood that the big endothelin may be introduced exogenously and that the activity would still occur, either on the cell surface or in the interior of the cell and that all such embodiments of the method would be encompassed by the scope and the spirit of the present claimed invention.

Another important embodiment of the present invention is a method of screening substances as effectors of endothelin converting enzyme. The discovery of the nucleic acid and amino acid sequences of the present invention provides a new and valuable method of screening naturally occurring and man made substances for their ability to inhibit ECE activity. By the use of the present invention, and particularly by the use of recombinant cells which express the ECE-1, a high throughput assay is possible for the first time. Of particular advantage will be the development of soluble forms of ECE based on the amino acid sequences disclosed herein. Such soluble enzymes will be essentially the hydrophilic regions of ECE that can be secreted into the extracellular medium and thus produced in greater quantity than is possible for a membrane bound enzyme. Such a soluble enzyme will be especially useful for expression in a prokaryotic host cell, such as an *E. coli* cell, for example.

This screening assay comprises obtaining a candidate substance which can come from any source. For example, it is proposed that compounds isolated from natural sources such as fungal extracts, plant extracts, bacterial extracts, higher eukaryotic cell extracts, or even extracts from animal sources, or marine, forest or soil samples, may be assayed for the presence of potentially useful pharmaceutical agents. In addition, man made substances would also be tested and would include, but are not limited to, synthetic compounds, peptides or other compounds designed de novo based on the predicted protein structure of the ECE. It is also understood that antibodies and other isolated or purified, but naturally occurring compounds could be screened by this process.

In the embodiment of the screening process involving a soluble ECE, the screening may be done in solution by standard assay methods. Activity would be determined by the concentration of ET in the presence or absence of a candidate substance. Concentration of ET produced might be determined by a sandwich immunoassay or by any other means.

In an alternative method, recombinant cells expressing ECE would be deposited on a surface such as the wells of a microtiter plate or in any suitable medium or container. A big endothelin substrate would also be present, either produced by the cells or supplied exogenously. Some distinguishable groups of cells would then be exposed to the candidate substance and some would not be so exposed under conditions effective to convert big ET-1 to ET-1. A measurement of the production of ET, would then be compared between cells which were or were not incubated with the candidate substance. A decrease in ET concentration over the control would indicate an inhibitor. Preferred cells to be used in the assay would be Chinese hamster ovary cells (CHO) for example, however, any cells which express the ECE would be acceptable and would be encompassed by the present claimed invention. Examples of other cell types include MDCK, $CaCo_2$, BHK, COS AND 293 cells.

Alternatively, candidate substances could be screened with the use of reporter genes under the control of endothelin converting enzyme promoters. In this embodiment, the reporter gene would be expressed in the presence and absence of a candidate substance as in the previously described screening assays. A change in level of the reporter gene product in the presence of the candidate substance relative to the level in the absence of the candidate substance would indicate an effector of ECE expression. Preferred reporter genes include, but are not limited to the β-galactosidase gene from *E. coli* and chloramphenicol acetyltransferase.

With the availability of a cDNA encoding an active endothelin converting enzyme, it is now possible to express large amounts of the enzyme in cultured cells. This ability will allow the molecular mechanism of the protease activity to be elucidated. This information will be crucial for the design of inhibitors and possibly useful mutations of the enzyme. The design and production of such mutant enzymes by site directed mutagenesis are well known in the art and such mutant enzymes would also be encompassed by the present claims.

BRIEF DESCRIPTION OF THE DRAWINGS

FIG. 1A–FIG. 1K. Nucleotide and deduced amino acid sequences of bovine ECE-1 cDNA. An in-frame stop codon that precedes the 5' ATG codon is marked by asterisks. An alternative poly (A) addition site is designated by an arrow. Fourteen sequences of Lys-C digested peptides from purified ECE-1 are underscored. The peptide sequence used for designing RT-PCR primers is marked by filled circles. The predicted transmembrane domain is designated by double underscoring. The zinc-binding motif (Jongeneel et al., 1989) is marked in bold. Predicted N-glycosylation sites are indicated by ‡. The nucleotide sequence is designated SEQ ID NO:1, the 60 base sequence preceding the second poly A site is designated SEQ ID NO:3, and the amino acid sequence is designated SEQ ID NO:2.

FIG. 1L. Topographical representation of the "NECK" (NEP-ECE-Kell) family of metalloproteases. Right hatched boxes, predicted transmembrane domains; left hatched boxes, zinc-binding motifs; N, N-glycosylation sites; Open circles, Cys residues; cross hatched boxes, regions of high sequence similarities. The scale indicates the number of amino acid residues.

FIGS. 2A–FIG. 2E. In vitro characterization of cloned ECE-1.

FIG. 2A. Functional expression of ECE-1 cDNA in transfected CHO cells. Total cellular homogenate was prepared from CHO/ECE-1 and untransfected CHO cells, and assayed for in vitro ECE activity in the absence and presence of 100 μM phosphoramidon.

FIG. 2B. Concentration-dependent inhibition of ECE-1 activity expressed in solubilized CHO/ECE-1 membranes by Phosphoramidon and FR901533.

FIG. 2C. pH profile of ECE-1 activity expressed in solubilized CHO/ECE-1 membranes.

FIG. 2D. Reconstitution of ECE-1 activity by metal ions after EDTA stripping. EDTA (30 μM) was added to solubilized CHO/ECE-1 membranes. After incubating on ice for 15 min, the designated concentrations of metal ions were added as chloride salt and ECE activity was measured.

FIG. 2E. Isopeptide selectivity of ECE-1 expressed in solubilized CHO/ECE-1 membranes. Designated synthetic big endothelin isopeptides (0.1 μM) were used as substrates and generation of corresponding mature peptides were measured by EIA.

FIG. 3. HPLC analysis of big ET-1 conversion by partially purified ECE-1 from CHO/ECE-1 cells. ECE-1 was partially purified from solubilized CHO/ECE-1 membranes by WGA-agarose chromatography as described in Example 1. The enzyme fraction (800 μg protein) was incubated at 37° C. with 1 μM big ET-1 in 800 μl of ECE assay buffer. After the designated time periods, 100-μl aliquots were removed from the reaction mixture and EDTA was added to the aliquots at 2.5 mM. The reaction mixture was separated by HPLC as described in Example 1. Arrows indicate elution times of the authentic peptides.

FIG. 4. Bioassay of culture supernatants from preproET-1-transfected CHO/ECE-1 cells using CHO cells expressing human $ET_A$ receptors as reporter cells. Sup-A and Sup-B represents the serum-free medium conditioned for 12 hours with CHO/ECE-1 and CHO cells each transiently transfected with the preproET-1 construct, respectively. Shown is a typical set of traces from three independent studies that gave similar results.

FIG. 5A. Effects of phosphoramidon and FR901533 on the secretion of big and mature ET-1 by preproET-1-transfected CHO/ECE-1 cells. □ and ■ indicate the levels of big and mature ET-1 in the absence of inhibitors, respectively, with a parallel culture of native CHO cells similarly transfected with the prepro ET-1 construct.

FIG. 5B. Effects of phosphoramidon and FR901533 on the production of mature ET-1 by 1:1 co-cultures of CHO/ECE-1 and CHO/preproET-1 cells. Results from parallel 1:1 co-cultures of untransfected CHO and CHO/preproET-1 cells are shown as a negative control (□,■).

FIG. 6A. Schematic representation of intracellular conversion of endogenously synthesized big ET-1 and its inhibition by phosphoramidon. Intracellular conversion is assumed to take place in the Golgi.

FIG. 6B. Cell-surface conversion of exogenously supplied big ET-1, and its inhibition by phosphoramidon and FR901533.

DETAILED DESCRIPTION OF THE PREFERRED EMBODIMENTS

Figure 1L:
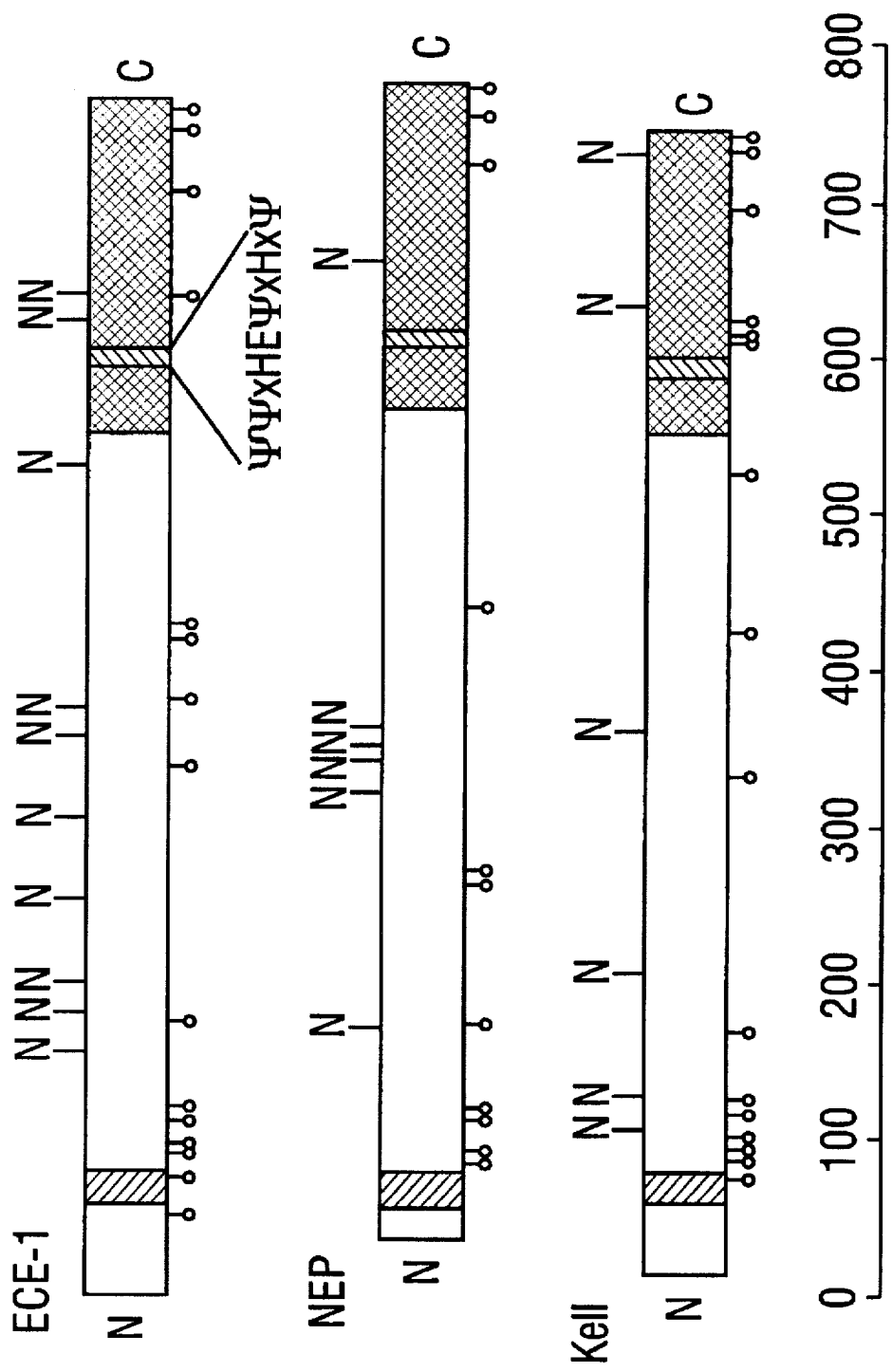

Since the initial prediction of its existence (Yanagisawa et al., 1988), ECE has been considered to be a potential site of the regulation of endothelin production, as well as a plausible target for therapeutic intervention in the endothelin system. However, research has been hampered by the elusive nature of the enzyme. The present disclosure provides the amino acid structure of the enzyme as well as the nucleic acid sequence. The physiological relevance of this form of the enzyme is indicated by: (i) The cloned ECE-1 cDNA provided a heterologous cell line that normally secretes only big ET-1 after transfection of a preproET-1 construct with the ability to secrete biologically active, mature ET-1. Over 50–90% of total endothelin was secreted as the mature peptide in a similar manner to that previously reported in cultured endothelial cells (Sawamura et al., 1991). (ii) The secretion of mature ET-1 by the ECE-1/preproET-1 double transfectants was inhibited by phosphoramidon, again in a manner similar to the inhibition previously observed in endothelial cells. (iii) In vitro analyses of cloned ECE-1 expressed in CHO cells demonstrated that it is a membrane-bound $Zn^{2+}$ metalloprotease with a neutral pH optimum, is capable of specifically cleaving the Trp21-Val22 bond of big ET-1, and is inhibited by phosphoramidon and FR901533 but not by thiorphan or captopril. These findings are consistent with the previously reported characteristics of the putative ECE in the crude membrane and purified preparations from vascular endothelium and other tissue sources (Ahn et al., 1992; Ohnaka et al., 1993; Takahashi et al., 1993; Waxman et al., 1993). (iv) The deduced structure of ECE-1 revealed a Type II membrane-bound $Zn^{2+}$ metalloprotease closely related to NEP and Kell protein. These structural features are well correlated with the proposed function of the enzyme. (v) ECE-1 mRNA was most abundantly expressed in vascular endothelial cells both in culture and in vivo. Considering the fact that vascular endothelium is the most abundant source of ET-1 in vivo, these findings are consistent with the expected tissue distribution of the enzyme.

The functional expression system for the cloned ECE disclosed herein has provided insights into several fundamental questions that have been controversial (Turner, 1993). For example, although both phosphoramidon and FR901533 efficiently inhibited the enzyme in vitro, only phosphoramidon was capable of inhibiting the secretion of mature ET-1 from live transfected cells that express both preproET-1 and ECE-1. Moreover, much higher concentrations of phosphoramidon were required to inhibit the conversion of endogenous big ET-1 in these cells, as compared with the concentrations required for the in vitro inhibition, a phenomenon observed by the inventors in cultured endothelial cells. Also, when a cell line expressing cloned ECE-1 but not preproET-1 was co-cultured with another cell line that expresses preproET-1 but not ECE-1, 5–10% of big ET-1 in the medium is converted to mature peptide. In contrast to the previous case, this conversion of exogenous big ET-1 was efficiently inhibited by both phosphoramidon and FR901533 added to the medium at low µM concentrations.

Figure 6B:
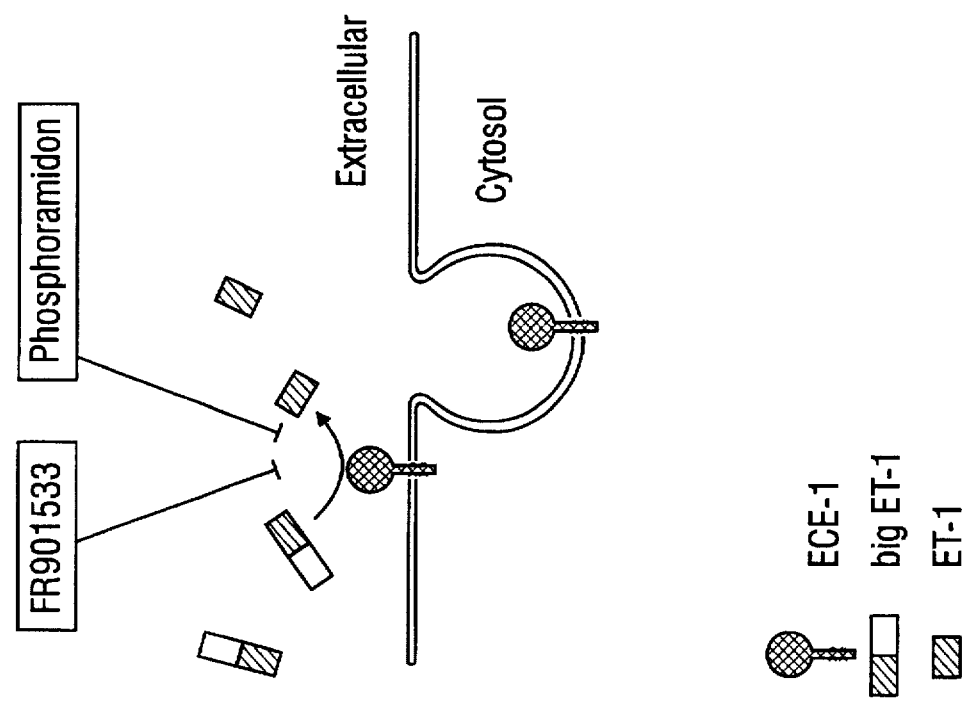
Figure 6A:
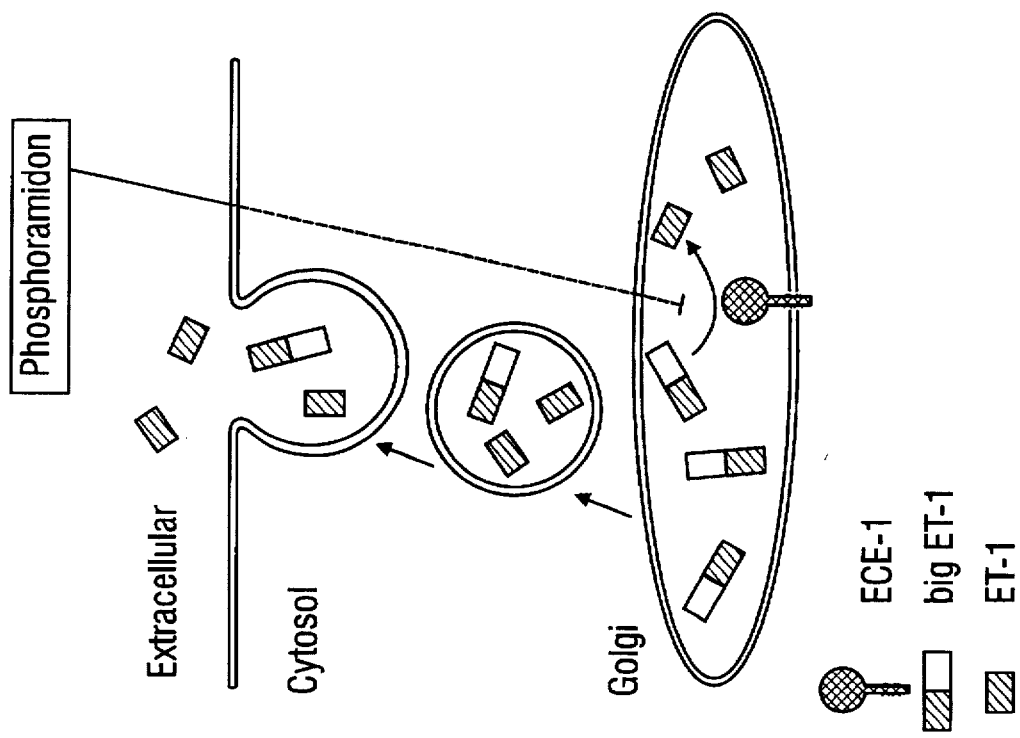

These findings leads to the following interpretation illustrated diagrammatically in FIG. 6A and FIG. 6B. In cells that express ECE-1, endogenously produced big ET-1 is converted to mature ET-1 within the cell, most likely during transit through the constitutive secretory pathway. Thus, FR901533 added from outside the cell cannot access the intracellular conversion site, while phosphoramidon, albeit inefficiently, enters the cells to inhibit the intracellular enzyme. The inventors have found that a major portion of ECE activity co-sediments with Golgi membranes in cultured endothelial cells, consistent with the present observations in the transfected cell line. A Golgi localization is consistent with the deduced structure of ECE-1, which predicts a Type II integral membrane protein with its putative catalytic domain facing inside the Golgi and secretory vesicles.

In addition, co-culture studies provide evidence that a portion of ECE-1 is expressed on the cell surface of the transfectants as an ecto-enzyme that is capable of cleaving the big ET-1 supplied from outside the cells. This apparent cell-surface conversion of exogenous big ET-1 was much less efficient (5–10% conversion) as compared with the intracellular conversion of endogenous big ET-1 (50–90% conversion). This is consistent with the previously reported inefficient (only up to a few %) phosphoramidon-sensitive conversion of exogenously administered big ET-1 in isolated perfused tissues and whole animal preparations (Opgenorth et al., 1992). Although the present invention does not rely on a single theory, the present disclosure supports the idea that the same ECE-1 molecule may account for both intracellular conversion of big ET-1 in ET-1-producing cells and cell-surface conversion of exogenously supplied big ET-1 on the target cells for ET-1 actions.

The apparent $K_m$ values of endothelial ECE have been reported to be in the 1–10 µM range both in crude membranes and purified enzyme preparations (Ahn et al., 1992; Ohnaka et al., 1993; Okada et al., 1990). Therefore, within the physiological concentrations of the substrate, the rate of conversion is approximately proportional to the substrate concentration. Therefore, the efficient conversion of endogenous big ET-1 within the secretory pathway may be at least partly due to the fact that the effective concentration of the substrate can be much higher intracellularly because of the spacial constraint. Even under the very conservative assumption that there is on average one molecule of big ET-1 per vesicle with an average diameter of 100 nm, the calculated concentration of big ET-1 is about 3 µM. In contrast, the concentration of big ET-1 in extracellular space would never exceed the range of low nM.

The present results show that ECE-1 converts big ET-1 more efficiently than big ET-2 and big ET-3. Taken in conjunction with the finding that vascular endothelium is the predominant expression site of ECE-1 mRNA, this isopeptide selectivity is teleologically consistent, since ET-1 is the only endothelin isopeptide produced in endothelial cells. It is contemplated that cell types that produce ET-2 and/or ET-3 express distinct isoenzyme(s) of ECE which are more selective towards big ET-2 and/or big ET-3. In situ hybridization studies have demonstrated that ECE-1 mRNA is abundantly expressed not only in vascular endothelium but also in a number of non-vascular cell types that have been demonstrated to be capable of producing ET-1 under certain stimuli, including adrenal (Imai et al., 1992) and pulmonary (Giaid et al., 1991b) epithelial cells, cardiac myocytes (Ito et al., 1993), and renal tubular epithelial cells (Ujiie et al., 1992). However, certain endothelin-producing cell types, most notably neurons (Giaid et al., 1991a), did not exhibit an expression of ECE-1 mRNA. These findings suggest the possibility that different ECE isoenzyme(s) may be expressed in neural tissues.

ECE-1, along with NEP and Kell protein, defines a new family of Type II membrane-bound metalloproteases (FIG. 1L). Kell protein is expressed on human red cells and other cell types, and carries the epitopes for the Kell minor blood group antigen (Lee et al., 1991b). Although its deduced structure clearly suggests that it is a metalloprotease, the actual protease activity has yet to be described for the Kell protein, and hence its physiological significance is totally unknown. In contrast, NEP has been well characterized as a major peptidase that degrades and inactivates various small peptide mediators, including opioids, atrial natriuretic peptides and endothelins (Roques et al., 1993; Vijayaraghaven et al., 1990). Although the structures of ECE-1 and NEP exhibit a striking similarity, these enzymes are remarkably different in terms of their substrate and cleavage site specificity. NEP cleaves many small peptides in a highly promiscuous manner, and its cleavage sites are only loosely defined as the N-terminal side of a hydrophobic amino acid residue (Roques et al., 1993; Turner, 1993). In fact, NEP rapidly degrades mature ET-1 itself at multiple internal cleavage sites (Vijayaraghaven et al., 1990). In contrast, ECE-1 is highly specific for the cleavage of Trp21-Val22 bond of big endothelins. Recent studies demonstrated that the C-terminal region of big ET-1(1-38) is essential for the peptide to act as a substrate for ECE (Ohnaka et al., 1993; Okada et al., 1993). The present disclosure extends these observations with the cloned ECE-1, and show that C-terminally truncated big ET-1(1-31) cannot be an ECE-1 substrate. These observations indicate that ECE-1 not only recognizes the primary structure of big ET-1 in the immediate vicinity of the cleavage site, but also discriminates a certain part of the tertiary structure of big ET-1. In view of the potential therapeutic intervention to the endothelin system at the level of ECE, this remarkable specificity of ECE-1 provides the potential opportunity that a selective inhibitor of the enzyme can interfere with mature ET-1 formation without disturbing other small peptide-mediated regulatory systems.

The isolation of the cDNA segment of the present invention will allow the expression of large quantities of the endothelin converting enzyme in various expression vectors and host cells. Examples of appropriate expression systems include, but are not limited to bacterial expression of recombinant plasmids and/or phage, recombinant baculovirus-infected insect cells and mammalian tissue culture cells such as Chinese hamster ovary (CHO) cells. The ECE cDNA may also be used for stable expression of the enzyme in transgenic animals such as mice.

Since the isolated cDNAs encompass the entire coding sequence, one may proceed to prepare an expression system for the preparation of recombinant endothelin converting enzyme. The engineering of DNA segment (s) for expression in a prokaryotic or a eukaryotic system may be performed by techniques generally known to those of skill in recombinant expression. It is believed that virtually any expression system may be employed in the expression of the endothelin converting enzyme.

Prokaryotic hosts may be preferred for expression of the ECE for some applications, and in particular for the expression of soluble forms of the enzyme. Some examples of prokaryotic hosts are various $E.\ coli$ strains, bacilli such as $Bacillus\ subtilis$, or other enterobacteriaceae such as $Salmonella\ typhimurium$ or $Serratia\ marcescens$, and various Pseudomonas species may be used, with $E.\ coli$ being the most preferred.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, a well known plasmid useful for transforming $E.\ coli$ is pBR322, a plasmid derived from an $E.\ coli$ species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda pGEM™-11 may be utilized in making a recombinant phage vector which can be used to transform host cells, such as $E.\ coli$ LE392. The most preferred prokaryotic vectors include pKK233-2, which utilizes the strong IPTG-inducible $P_{trc}$ promoter and the pT7 series which utilize the T7 RNA polymerase promoter system.

Some promoters commonly used in recombinant DNA construction include the B-lactamase (penicillinase) and lactose promoter systems, as well as viral promoters. While these are the most commonly used, other microbial promoters have been discovered and utilized, and details concerning their nucleotide sequences are readily available, enabling a skilled worker to ligate them functionally into plasmid vectors.

In addition to prokaryotes, eukaryotic microbes, such as yeast cultures may also be used. $Saccharomyces\ cerevisiae$, or common baker's yeast is a commonly used eukaryotic microorganism, although a number of other strains are available. For expression in Saccharomyces, the plasmid YRp7, for example, may be used. This plasmid contains the trpl gene which provides a selection marker for a mutant strain of yeast lacking the ability to grow in tryptophan. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the expressed sequence to provide polyadenylation of the mRNA and termination. Other promoters, which have the additional advantage of transcription controlled by growth conditions are the promoter region for alcohol dehydrogenase 2, iso-cytochrome C, acid phosphatase, degradative enzymes associated with nitrogen metabolism, the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

Of particular interest is the use of insect cells as a host for baculoviral expression vectors. Currently, the preferred baculovirus expression systems utilize the lytic insect virus known as *Autographa californica* multiply enveloped nuclear polyhedrosis virus. For production of recombinants in insect cells using recombinant baculoviral vectors, it is desirable to utilize the polyhedron gene's powerful promoter and control sequences. This can be accomplished by replacing the baculoviral polyhedron gene with the cDNA to be expressed. Baculoviral expression vectors ordinarily include all the original baculoviral genes except the polyhedron gene and may include additional marker genes such as the β-galactosidase gene. Examples of such useful baculoviral preparations include Linearized AcMNPV Baculovirus DNA, Linearized AcRP23. lacZ Baculovirus DNA, and Linearized AcUW1. lacZ Baculovirus DNA. After cloning the cDNA to be expressed in a suitable transfer plasmid, the cDNA can be transferred in place of the baculovirus polyhedron gene by the process of recombination. The transfer plasmids contain baculoviral DNA sequences to promote the recombination with linear baculoviral DNA and may also contain additional marker genes such as the β-galactosidase gene. Suitable transfer plasmids include pBlueBac III, pBlueBacHis, and pAcUW21. The recombination to assemble the recombinant baculovirus which expresses the cDNA of interest and production of the protein product from that cDNA is performed in insect cells or insect hosts. Examples of suitable host cells include *Spondoptera frugiperda* Sf9 cells, Sf21 cells, and MG1 cells.

In addition to microorganisms and insects, cultures of cells derived from vertebrate organisms may also be used as hosts. In principle, any such vertebrate or invertebrate cell culture is workable. However, vertebrate cells are a preferred host, and propagation of vertebrate cells in culture (tissue culture) has become a routine procedure in recent years. Examples of such useful host cell lines are VERO and HeLa cells, Chinese hamster ovary (CMO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, cytomegalovirus, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

It is understood in the art that to bring a coding sequence under the control of a promoter, one positions the 5' end of the transcription initiation site of the transcriptional reading frame of the protein between about 1 and about 50 nucleotides "downstream" of (i.e., 3' of) the chosen promoter. In addition, where eukaryotic expression is contemplated, one will also typically desire to incorporate into the transcriptional unit which includes the ECE protein, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that the endothelin converting enzyme of the invention may be "overexpressed", i.e., expressed in increased levels relative to its natural expression in endothelial cells, or even relative to the expression of other proteins in the recombinant host cell. Such overexpression may be assessed by a variety of methods, including radiolabelling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural endothelial cells is indicative of overexpression, as is a relative abundance of the specific protein in relation to the other proteins produced by the host cell as determined, e.g. by visibility on a gel.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

Amino Acid Segments

An important embodiment of the amino acid sequences of the present invention is the use of the ECE amino acid sequence to model the protein structure for use in inhibitor design, for example. Initially, this entails a comparison of the protein sequence disclosed herein with the sequences of related proteins to predict transmembrane regions, zinc binding regions and even the protease catalytic site. In this way, the transmembrane domains and the putative glycosylation sites have been determined. Also, by comparing the amino acid sequence of the present disclosure with proteins of similar function (membrane bound metalloproteases) sequences may be identified which are directly involved in those functions. In particular, amino acid residues which are conserved over a range of species are good candidates for involvement in functional active sites or binding sites. The amino acid sequence of the endothelin converting enzyme will thus be useful for designing superior inhibitors. For example, potential inhibiting substances can be tested for binding to amino acid segments known to be involved in various functions of the protease, and would thus be screened for potential inhibition of activity.

An alternate use of the ECE protein sequence will be to model the protein structure for use in designing compounds as vehicles for drug targeting. For example, analogs of big endothelin may be designed and used as targeting agents to direct drug delivery specifically to the endothelium.

Production of Antibodies

Another important embodiment of the amino acid sequences of the ECE-1 is their use in the production of antibodies. This amino acid sequence may be used to synthesize peptide antigens for monospecific antibody development. Antibodies, both polyclonal and monoclonal, specific for the endothelin converting enzyme of the present invention may be prepared using conventional immunization techniques, as will be generally known to those of skill in the art. A composition containing antigenic epitopes of the ECE protein can be used to immunize one or more experimental animals which will then proceed to produce specific antibodies against ECE. Typically an animal used for production of antisera is a rabbit, a mouse, a rat, a hamster or a guinea pig. Because of the relatively large blood volume of rabbits, a rabbit is a preferred choice for production of polyclonal antibodies. Polyclonal antisera may be obtained, after allowing time for antibody generation, simply by bleeding the animal and preparing serum samples from the whole blood.

As is well known in the art, a given polypeptide may vary in its immunogenicity. It is often necessary therefore to couple the immunogen (e.g. a polypeptide of the present invention) with a carrier. Exemplary and preferred carriers are keyhole limpet hemocyanin (KLH), Purified Peptide Derivative of Tuberculin (PPD) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used in the production of polyclonal antibodies depends inter alia, upon the nature of the immunogen as well as the animal used for immunization. A variety of routes can be used to administer the immunogen (subcutaneous, intramuscular, intradermal, intravenous and intraperitoneal). The production of polyclonal antibodies is monitored by sampling blood of the immunized animal at various points following immunization. When a desired level of immunogenicity is obtained, the immunized animal can be bled and the serum isolated and stored.

A monoclonal antibody of the present invention can be readily prepared through use of well-known techniques such as those exemplified in U.S. Pat. No 4,196,265, incorporated herein by reference. Typically, a technique involves first immunizing a suitable animal with a selected antigen (e.g. a polypeptide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell, and a more preferred cell line is the NS1/1 Ag 4.1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptide. The selected clones can then be propagated indefinitely to provide the monoclonal antibody.

By way of specific example, to produce an antibody of the present invention, mice are injected intraperitoneally with about 1–200 µg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g. at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established. Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in selection medium such as HAT media (hypoxanthine, aminopterin, thymidine). Unfused myeloma cells lack the enzymes necessary to synthesize nucleotides from the salvage pathway and are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides of the invention can be recognized as antigens, and thus identified. Once identified, those polypeptides can be isolated and purified by techniques such as antibody-affinity chromatography. In antibody-affinity chromatography, a monoclonal antibody is bound to a solid substrate and exposed to a solution containing the desired polypeptide. The polypeptide-antigen is removed from the solution through an immunospecific reaction with the bound antibody. The polypeptide is then easily removed from the substrate and purified.

It is proposed that the monoclonal antibodies of the present invention will find useful application in standard immunochemical procedures, such as ELISA and western blot methods, as well as other procedures which may utilize antibody specific to ECE-1 epitopes. Additionally, it is proposed that monoclonal antibodies specific to the particular ECE-1 may be utilized in other useful applications. For example, their use in immunoabsorbent protocols may be useful in purifying native or recombinant endothelin converting enzymes from various species or variants thereof. A particularly useful application of such antibodies is in purifying native or recombinant endothelin converting enzymes, for example, using an antibody affinity column. Such antibodies would also be useful as immunohistochemical or immunoblotting reagents in the diagnosis of hypertension and related diseases. The operation of all such immunological techniques will be known to those of skill in the art in light of the present disclosure.

Nucleic Acid Hybridization

The DNA sequences disclosed herein will find utility as probes or primers in nucleic acid hybridization embodiments. As such, it is contemplated that oligonucleotide fragments corresponding to the sequences of SEQ ID NO:1 for stretches of between about 17 nucleotides to about 30 nucleotides will find particular utility, with even longer sequences, e.g. 40, 50, 100, even up to full length, being more preferred for certain embodiments. The ability of such nucleic acid probes to specifically hybridize to endothelin converting enzyme-encoding sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100 nucleotides or so, complementary to SEQ ID NO:1 or SEQ ID NO:3 will also have utility as hybridization probes. These probes will be useful in a variety of hybridization embodiments, such as Southern and northern blotting in connection with analyzing ECE structural or regulatory genes in diverse tissues and in various species. The total size of the fragment, as well as the size of the complementary stretches, will ultimately depend on the intended use or application of the particular nucleic acid segment. Smaller fragments will generally find use in hybridization embodiments, wherein the length of the complementary region may be varied, such as between about 17 and about 100 nucleotides, or even up to 2889 according to the complementary sequences one wishes to detect.

The use of a hybridization probe of about 17 nucleotides in length allows the formation of a duplex molecule that is both stable and selective. Molecules having complementary sequences over stretches greater than 17 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (incorporated herein by reference) or by introducing selected sequences into recombinant vectors for recombinant production.

Accordingly, the nucleotide sequences of the invention may be used for their ability to selectively form duplex molecules with complementary stretches of ECE genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g. one will select relatively low salt and\or high temperature conditions, such as provided by 0.02M–0.15M NaCl at temperatures of 50° C. to 70° C. Such selective conditions tolerate little, if any, mismatch between the probe and the template or target strand.

Preferred hybridization conditions and temperatures include a solution containing 50% (volume/volume) formamide, 5× Denhardt's solution, 6× SSC, 0.1% (weight/volume) SDS, and 100 µg/ml salmon sperm DNA, and 1 mM sodium pyrophosphate at 37° C. For nucleotide sequences longer than 50 nucleotides, preferred wash conditions include a solution containing 2× SSC/0.5% SDS at 25° C. for 30 min followed by one or more washes in a solution containing 0.2× SSC/0.5% SDS at 60° C. for 30 min per wash. For nucleotide sequences shorter than 50 nucleotides, preferred wash conditions include a solution containing 2× SSC/1% SDS at 25° C. for 30 min followed by one or more washes in a solution containing 2× SSC/1% SDS at 50° C. for 30 min.

Of course, for some applications, for example, where one desires to prepare mutants employing a mutant primer strand hybridized to an underlying template or where one seeks to isolate endothelin converting enzyme-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the circumstances based on the particular criteria required (depending, for example, on the G+C contents, type of target nucleic acid, source of nucleic acid, size of hybridization probe, etc.). Following washing of the hybridized surface to remove nonspecifically bound probe molecules, specific hybridization is detected, or even quantified, by means of the label.

Longer DNA segments will often find particular utility in the recombinant production of peptides or proteins. DNA segments which encode peptide antigens from about 15 to about 50 amino acids in length, or more preferably, from about 15 to about 30 amino acids in length are contemplated to be particularly useful, as are DNA segments encoding entire ECE proteins. DNA segments encoding peptides will generally have a minimum coding length on the order of about 45 to about 150, or to about 90 nucleotides. DNA segments encoding full length proteins may have a minimum coding length on the order of about 2274 nucleotides for a protein in accordance with SEQ ID NO:2.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular nucleic acid and amino acid sequences of SEQ ID NOS:1–5. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

DNA segments encoding an ECE gene may be introduced into recombinant host cells and employed for expressing an ECE protein. Alternatively, through the application of genetic engineering techniques, subportions or derivatives of selected ECE genes may be employed. Equally, through the application of site-directed mutagenesis techniques, one may re-engineer DNA segments of the present invention to alter the coding sequence, e.g., to introduce improvements to the antigenicity of the protein or to test for binding site mutants in order to examine protease activity at the molecular level. Where desired, one may also prepare fusion peptides, e.g., where the ECE coding regions are aligned within the same expression unit with other proteins or peptides having desired functions, such as for immunodetection purposes.

In a further embodiment, the nucleic acid sequences of the present invention may be used to synthesize anti-sense or ribozyme probes to down-regulate expression of the endothelin converting enzyme in the endothelium for use as vasoconstrictor control agents. For example, an anti-sense probe that is designed to hybridize to the mRNA synthesized from the ECE gene would, when introduced into the endothelial cells, disrupt translation of the mRNA and would hence lower the expression of the ECE protein. The lowered levels of ECE would function to lower mature endothelin levels.

Screening Assays

In still further embodiments, the present invention concerns a method for identifying new endothelin converting enzyme inhibitory compounds, which may be termed as "candidate substances." It is contemplated that this screening technique will prove useful in the general identification of any compound that will serve the purpose of inhibiting endothelin maturation. It is further contemplated that useful compounds in this regard will in no way be limited to pre-endothelin analogs.

Accordingly, in screening assays to identify pharmaceutical agents which affect endothelin maturation, it is proposed that compounds isolated from natural sources such as fungal extracts, plant extracts, bacterial extracts, higher eukaryotic cell extracts, or even extracts from animal sources, or marine, forest or soil samples, may be assayed for the presence of potentially useful pharmaceutical agents. It will be understood that the pharmaceutical agents to be screened could also be derived from chemical compositions or man-made compounds. In important aspects, the candidate substances may be anti-ECE antibodies, including polyclonal and monoclonal antibodies. The suspected agents could also include proteins and peptides, such as those derived from recombinant DNA technology or by other means, including peptide synthesis. The active compounds may include fragments or parts of naturally-occurring compounds or may be only found as active combinations of known compounds which are otherwise inactive.

To identify a candidate substance capable of inhibiting ECE proteolytic activity, one would first obtain a recombinant cell line capable of expressing ECE or would obtain a soluble form of ECE. Naturally, one would measure or determine the activity of the ECE protease in the absence of the added candidate substance. One would then add the candidate substance to the assay mix or cell growth media or one would expose the cells in an appropriate way to the candidate substance and re-determine the ability of the cells to produce mature endothelin in the presence of the candidate substance. A candidate substance which reduces the activity of the ECE protease relative to the activity in its absence is indicative of a candidate substance with inhibitory capability. The indicator in the screening assays will preferably be mature endothelin.

In the most preferred embodiment, stably transfected ECE over-expressing cell lines will be used for high throughput assays to screen synthetic compounds, fungal extracts, plant extracts, bacterial extracts, higher eukaryotic cell extracts or others as mentioned above, for potential inhibitors of the ECE activity. In addition, these various extracts will be screened for use in the treatment of disorders such as high blood pressure, kidney failure and certain forms of stroke.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Purification and cDNA Cloning of ECE

Reagents

Human ET-1(1-21), human big ET-1(1-38) and human big ET-1(22-38) were obtained from American Peptides. Phosphoramidon, thiorphan, captopril, 1,10-phenanthroline, phenylmethylsulphonyl fluoride (PMSF), 4-amidinophenylmethylsulphonyl fluoride (APMSF), p-chloro-mercuriphenylsulphonic acid (pCMS), N-ethylmaleimide (NEM), E-64, pepstatin A, chymostatin, leupeptin, n-octylglucoside, and polyoxyethylene-10-lauryl ether ($C_{12}E_{10}$) were from Sigma. Fura-2/AM was from Molecular Probes. FR901533 (WS79089B; 1,6,9,14-tetrahydroxy-3-(2-hydroxypropyl)-7-methoxy-8,13-dioxo-5,6,8,13-tetrahydro-benzo[a]naphthacene-2-carboxylate Na) and FR139317 was a gift from Fujisawa Pharmaceutical Co., Ltd. For measurement of FR901533 concentration in culture medium, the samples were injected onto a $C_{18}$ reverse-phase HPLC column, which was equilibrated and isocratically eluted with 75% (v/v) methanol/0.1% (v/v) trifluroacetic acid (TFA) at a flow rate of 1 ml/min. FR901533 was detected as an isolated peak of 245-nm absorbance with an elution time of 9 min.

Measurement of ECE Activity

Reaction mixtures for ECE assay (50 µl) contained 0.1M sodium phosphate buffer (pH 6.8), 0.5M NaCl, 0.1 µM human big ET-1(1-38) and enzyme fraction. For some studies, the reactions were preincubated at 37° C. with various protease inhibitors for 15 minutes prior to the addition of big ET-1. The reactions were incubated at 37° C. for 30 min in siliconized 0.5-ml microcentrifuge tubes. Enzyme reactions were terminated by adding 50 µl of 5 mM EDTA. The reactions were then directly assayed for mature ET-1(1-21) as previously described (Suzuki et al., 1989). Duplicate assay wells were used for each enzyme reaction. Protein concentration was determined by the Bradford method (Bio-Rad) using IgG as standard.

Reverse-Phase HPLC of Endothelin Peptides

Samples were injected into a $C_{18}$ reverse-phase HPLC column (Ultrasphere ODS 5 µm, 4.6×250 mm; Beckman), which was eqhilibrated with 18% (v/v) acetonitrile/0.1% (v/v) TFA and maintained at 40° C. The column was eluted at a flow rate of 1 ml/min with an 18–30% linear gradient of acetonitrile in 0.1% TFA over 12 minutes followed by a 30–36% linear gradient over an additional 12 minutes. Peptides were detected by UV absorbance at 210 nm. Synthetic ET-1(1-21), human big ET-1(1-38) and human big ET-1(22-38) eluted at 23 minutes, 21 minutes and 8.5 minutes, respectively. To confirm chemical authenticity of immunoreactivity in culture supernatants, the conditioned medium was pre-extracted with a Sep-Pak $C_{18}$ cartridge as described (Suzuki et al., 1989) before HPLC. HPLC fractions (0.5 ml) were collected and evaporated to dryness under vacuum. Dried residue from each fraction was reconstituted in EIA buffer (Suzuki et al., 1989) and subjected to big and mature ET-1 assay. More than 90% of the immunoreactive big and mature ET-1 contained in the original medium was consistently recovered as single peaks eluted at 21 minutes and 23 minutes, respectively. No other immunoreactive peaks were detected.

Purification of ECE

Bovine adrenal glands were obtained at a local slaughter house, immediately immersed in ice-cold Dulbecco's phosphate buffered saline (PBS), and brought to the laboratory within 2 hours. All subsequent procedures were performed at 4° C. Adrenal cortices were carefully separated from the medulla and connective tissue. The cortices (≈80 per batch) were minced by a food processor and immediately homogenized in 4×volume of buffer A (20 mM Tris-HCl (pH 7.4)/20 µM pepstatin A/1 mM PMSF/1 mM NEM) containing 250 mM sucrose by a Polytron homogenizer at 10,000 r.p.m. for 3×15 sec. The homogenate was centrifuged at 1,000×g for 10 min, and the resulting supernatant was further centrifuged at 100,000×g for 60 min. The pellet was resuspended in 5×volume of buffer A by a Teflon homogenizer, and centrifuged again at 100,000×g for 60 min. The crude membrane pellet was solubilized at 10–20 mg protein/ml in buffer A containing 2.5% $C_{12}E_{10}$ for 30 min. The mixture was centrifuged at 100,000×g for 60 min, and the supernatant was saved as solubilized membrane.

The purification scheme was partly based on a published procedure (Takahashi et al., 1993). Solubilized membrane was applied to a DEAE column (DEAE Toyopearl 650S, 2.6×20 cm; Toso-Haas) preequilibrated with 20 mM Tris-HCl (pH 7.4) containing 0.1% $C_{12}E_{10}$. The column was eluted at a flow rate of 3 ml/min with a linear gradient of 0–0.5M NaCl in 400 ml of the same buffer. The active fractions were pooled and loaded to a wheat-germ agglutinin (WGA) agarose column (2.6×9.5 cm; Seikagaku U.S.A.) equilibrated with 20 mM Tris-HCl (pH 7.4)/0.15M NaCl/0.015% $C_{12}E_{10}$. The column was washed at a flow rate of 0.5 ml/min with 100 ml of the same buffer, and eluted with the same buffer containing 50 mg/ml N-acetylglucosamine. The active fractions were applied at a flow rate of 0.5 ml/min to a zinc chelating column (Chelating Sepharose FF, 1.6×8.5 cm; Pharmacia) preequilibrated with 20 mM Tris-HCl (pH 7.4)/0.15M NaCl/0.015% $C_{12}E_{10}$. The flow-through fractions containing ECE activity from the zinc chelating column were loaded at a flow rate of 0.5 ml/min to a Blue-B dye agarose column (1.6×10 cm; Amicon) equilibrated with 20 mM Tris-HCl (pH 7.4)/1M NaCl/0.015% $C_{12}E_{10}$. After washing the column with 100 ml of the same buffer, the column was connected to a WGA-agarose column (1.6×6.5 cm) and then eluted at a flow rate of 0.2 ml/min with 150 ml of 3M NaCl/1M 20 mM Tris-HCl (pH 7.4)/0.015% $C_{12}E_{10}$. The WGA column was disconnected and equilibrated at a flow rate of 0.2 ml/min with 140 ml of 20 mM Tris-HCl (pH 7.4)/0.15M NaCl/25 mM n-octylglucoside. The column was eluted with 40 ml of the same buffer containing 50 mg/ml N-acetylglucosamine at a flow rate of 0.2 ml/min. The active fractions were pooled, diluted 2 fold and applied to a Mono Q HR 5/5 column (Pharmacia) equilibrated with 20 mM BisTris-HCl (pH 7.0)/25 mM n-octylglucoside. The column was eluted at a flow rate of 1 ml/min with a linear gradient of 0–0.5M NaCl in 30 ml of the same buffer.

Cell culture

CHO-L1 cells were cultured in monolayers in Ham's F-12/DMEM (1:1 mix) medium supplemented with 10% (v/v) fetal bovine serum (FBS; HyClone) in a humidified atmosphere of 5% $CO_2$/95% air at 37° C. Endothelial cells were isolated from bovine coronary arteries by collagenase treatment as described (Rosolowsky and Campbell, 1994), and cultured in DMEM containing 10% (v/v) FBS. Cells were identified as endothelial cells by the typical cobblestone appearance of monolayers and by positive immunostaining of Factor VIII antigen. Since most batches of tissue culture-grade trypsin preparations were contaminated with large amounts of metalloproteases with ECE-like activities, a highly purified crystallized preparation of trypsin (Sigma, Cat. No. T7418) was used for most tissue culture procedures disclosed herein.

Preparation of CHO membranes

Approximately 3,000-cm$^2$ confluent monolayers of cells ($\approx 10^8$ cells) were rinsed twice with ice-cold PBS. Cells were scraped off by a rubber policeman in ice-cold PBS, and collected by centrifugation. All subsequent procedures were performed at 4° C. Cells were resuspended in 10×volume of buffer B (20 mM Tris-HCl (pH 7.4)/20 µM pepstatin A/1 mM PMSF/1 MM pCMS/250 mM sucrose), and homogenized by a 30-ml Teflon homogenizer with the piston rotating at 300 r.p.m. Solubilized membranes were prepared from this homogenate as described under Purification of ECE, except that buffer B was used instead of buffer A. For protease inhibitor studies, membranes were prepared by using buffer B without pepstain A, PMSF and pCMS.

Results

ECE activity was assayed in vitro by incubating enzyme fractions with synthetic human big ET-1 and measuring the generation of mature ET-1 by a sandwich-type enzyme immunoassay (EIA) that does not crossreact with the substrate big ET-1 (Suzuki et al., 1989). After screening various mammalian tissues as a suitable starting material for the purification of ECE, membrane fractions from bovine adrenal cortex were found to contain a large amount of ECE activity (specific activity of detergent-solubilized membrane fraction: ≈13 pmol/hr/mg protein at 0.1 µM big ET-1, which was similar to endothelial cell membranes under these assay conditions). This activity was inhibited >90% by 1 mM EDTA or 100 µM phosphoramidon, but not by 100 µM thiorphan or by inhibitors of other classes of proteases. A maximum activity was obtained at pH 6.8 in sodium phosphate buffer. These profiles were similar to the previously reported properties of the putative endothelial ECE (Ahn et al., 1992; Ohnaka et al., 1993; Okada et al., 1990). Moreover, the adrenal cortex membrane preparations are low in metalloprotease activities that further degrade mature ET-1. These preliminary findings led to bovine adrenal cortex as the starting material. By using a purification scheme partly based on published methods (Takahashi et al., 1993), this membrane-bound ECE activity was purified to near homogeneity, which resulted in the enrichment of about 3,000-fold in specific activity. SDS-polyacrylamide gel electrophoresis of the purified enzyme fraction showed a single band with an apparent molecular mass of about 126 KD; the intensity of this band was closely correlated with ECE activity after anion exchange and gel filtration chromatography. Approximately 400 pmol of purified ECE protein was obtained from 320 adrenal cortices.

EXAMPLE 2

Sequencing of ECE-1 cDNA

Microsequencing of purified ECE

Active fractions from the final Mono Q column (≈400 pmol ECE) were precipitated in 5×volume of acetone at −20° C. and separated on a 4–15% gradient SDS-polyacrylamide gel under reduced conditions. The protein bands were electroblotted onto a polyvinylidene difluoride membrane, and stained with Coomassie Brilliant Blue. The membrane region containing the 126-KD ECE band was excised and subjected to solid-phase Lys-C digestion (Fernandez et al., 1992). Peptides released from the membrane were separated by an Applied Biosystems model 130A HPLC (Applied Biosystems RP-300 C$_8$ column, 2.1×100 mm). The first separation was performed in 0.1% (v/v) TFA with a gradient of 0–70% (v/v) acetonitrile over 100 min at a flow rate of 50 µl/min. Some of the individual peaks from this separation were re-loaded on the same column and further separated using the same acetonitrile gradient with 0.1% ammonium acetate instead of TFA. Peptides were sequenced on Applied Biosystems model 470A and 477A sequencers.

RT-PCR

RNA was extracted from bovine adrenal cortex by the guanidinium/CsCl method (Sakurai et al., 1990), and poly (A)$^+$ RNA was enriched by oligo (dT) cellulose chromatography. First strand cDNA synthesis was carried out with 2 µg poly (A)$^+$ RNA and oligo(dT)$_{12-16}$ primers by using SuperScript reverse transcriptase (Gibco/BRL) as recommended by the manufacturer. The first PCR reaction contained 60 mM Tris-HCl (pH 8.5), 15 mM (NH$_4$)$_2$SO$_4$, 3.5 mM MgCl$_2$, 0.25 mM each dNTP, 10% (v/v) DMSO, 7.5 pmol each of degenerative primers GAGAAGCTTCCNGA(A/G)AT(A/C/T)GTNTT(C/T)CC, SEQ ID NO:4 and GAGATCGATAA(A/G)TT(C/T)AANGC(A/G)TTNGG, SEQ ID NO:5, 10 ng first-strand cDNA, and 2.5 U Taq DNA polymerase. The initial 5 cycles were carried out at an annealing temperature of 37° C. and then 30 more cycles were done at 47° C. The PCR products were separated through a 4% agarose gel, a 90–110 bp region was excised from the gel and the DNA was extracted. The second PCR was performed with one tenth of the extracted DNA as template under the same conditions at an annealing temperature of 50° C. for 30 cycles. The resultant 92-bp product was subcloned into pCR™II plasmid vector (Invitrogen).

cDNA library screening

λgt10 cDNA libraries were constructed by using the SuperScript kit (Gibco/BRL) against poly(A)$^+$ RNA from bovine adrenal cortex, lung, and cultured coronary artery endothelial cells. Approximately 1×10$^6$ plaques from each unamplified library were screened with random-primed $^{32}$P-labeled RT-PCR product as probe. Fifteen, 30 and ≈400 positive plaques were identified in the adrenal cortex, lung, and endothelial cell libraries, respectively. Out of these clones, 10, 3 and 4 longer clones from the respective libraries were plaque-purified and subjected to further analysis.

DNA Sequencing

Overlapping restriction fragments of cDNA were subcloned in pBluescript plasmid vector (Stratagene), and double-stranded plasmid DNA were PCR-sequenced by an Applied Biosystems model 373A DNA Sequenator. Both strands of cDNA were covered at least twice.

Northern blots

RNA was extracted from bovine tissues by the LiCl/urea method (Inoue et al., 1989b). Total RNA (10 µg) was separated in a formaldehyde/1.1% agarose gel, transferred to a nylon membrane, and hybridized in QuickHyb solution (Stratagene) as recommended by the manufacturer. Random-primed riP-labeled cDNA inserts (≈2-Kb) encoding bovine ECE-1 and β-actin were used as probes. The membranes were washed in 0.1×SSC/0.1% SDS at 60° C., and exposed to an X-ray film for 90 min at −80° C. with a screen.

Results

The N-terminal sequences of Lys-C-digested peptide fragments from the 126-KD ECE band were determined. Although all microsequences were novel, one of them (residues 562–586 in FIG. 1G) showed a significant similarity to amino acid residues 543–567 from the published sequence of human NEP, a known membrane-bound metalloprotease (Malfroy et al., 1988). A pair of highly degenerate oligonucleotide primers were designed based on this 25-residue sequence and cDNA products of the predicted size were obtained by reverse transcriptase (RT)-PCR from bovine adrenal cortex RNA. The nucleotide sequence of the cloned 75-bp cDNA insert encoded the peptide sequence exactly. With this RT-PCR product as a probe, cDNA libraries from bovine adrenal cortex, lung and cultured coronary artery endothelial cells were screened. Several positive clones from each library were purified and sequenced, and the overlapping nucleotide sequences of all of these clones were confirmed to be identical, indicating they are derived from the same mRNA species. The nucleotide sequences of the longest ECE-1 cDNAs from each tissue had a 5' ATG triplet which was preceded by an in-frame stop codon and followed by a long open reading frame. The encoded amino acid sequence of ECE-1 from this initiator Met codon is shown in FIG. 1A–FIG. 1I.

EXAMPLE 3

Structure of ECE-1

The ECE-1 cDNA encodes a novel 758-amino acid polypeptide. The sequence accommodates all of the 14 sequences determined from the Lys-C digests of the purified protein, all of which are preceded by a Lys residue in the encoded sequence, confirming that ECE-1 cDNA encodes the purified protein (FIG. 1A–FIG.1I underlines). The predicted ECE-1 protein has no apparent N-terminal signal sequence. Instead, there is a single putative transmembrane helical domain of 21 amino acids. This predicts a Type II integral membrane protein with a 56-residue N-terminal cytoplasmic tail and an extracellular C-terminal of 681 amino acid residues that contains the catalytic domain (FIG. 1L).

Amino acid residues 592–601 of ECE-1 match the highly conserved consensus sequence of a zinc-binding motif, ψψXHEψXHXψ (where ψ represents a hydrophobic amino acid residue), that is shared by all known $Zn^{2+}$ metalloproteases (Jongeneel et al., 1989). In this motif, the two invariant His residues are believed to chelate the metal ion, whereas the invariant Glu residue provides an essential carboxyl group in the active center of the enzyme. A Lipman-Pearson search of the current Entrez sequence database detected a significant similarity of the ECE-1 sequence to NEP (Malfroy et al., 1988) and the human Kell minor blood group protein (Lee et al., 1991b) (FIG. 1L). The sequence similarity is especially high within the C-terminal one third of the putative extracellular domain, which includes the region around the zinc-binding motif. Within the regions represented by right hatched boxes in FIG. 1L, ECE-1 exhibits 58% and 36% amino acid identities to NEP and Kell, respectively. In contrast, the N-terminal of ECE-1 resembles NEP and Kell only slightly.

The ECE-1 protein has 10 predicted sites for N-glycosylation in the extracellular domain. This is consistent with the observation that ECE behaves as a highly glycosylated protein (Ohnaka et al., 1993; Takahashi et al., 1993; Waxman et al., 1993). The predicted molecular weight of the polypeptide chain is 65,614. The difference between this value and the apparent molecular weight of ECE-1 on SDS-polyacrylamide gel may be largely due to the sugar side chains. Four Cys residues are conserved among all 3 proteins in the extracellular domain near the transmembrane helix (FIG. 1L). These Cys residues are reported to be essential for the native conformation of NEP and are thought to form intra- or inter-chain disulfide bonds (Roques et al., 1993).

EXAMPLE 4

Properties of Cloned ECE-1 Expressed in Heterologous Cells

Expression constructs and transfection

The entire coding regions from bovine ECE-1, human preproET-1 (Inoue et al., 1989b), and human $ET_A$ receptor (Sakamoto et al., 1993) cDNAs were subcloned into pME18Sf-expression vector (Sakamoto et al., 1993). These constructs (8 µg) were co-transfected with 0.4 µg of pSV2neo into CHO-K1 cells as described (Chen and Okayama, 1987). G418 (1 mg/ml) resistant colonies were isolated by trypsinization in a cloning cup, and the monoclonal cell lines that express the highest levels of the respective products were chosen. Transient transfection of the preproET-1 cDNA was performed by the DEAE-dextran method as described (Sakurai et al., 1990). Twelve hours after transfection, cells were refed with fresh medium with or without ECE inhibitors. The medium was conditioned for an additional 12 hours and directly subjected to EIA for mature and big ET-1 (Suzuki et al., 1990; Suzuki et al., 1989). For the $Ca^{2+}$ transient bioassay (see below), Phenol Red-free CHO-SFM medium (Gibco/BRL) without serum was used in order to avoid artefacts induced by serum and the dye.

Results

In a search for a transfection-competent cell line that has minimal endogenous ECE activity, it was found that many commonly used cell lines (including monkey COS, mouse L and 3T3, and human 293 cells) secrete considerable amounts of mature ET-1 when transfected with a human preproET-1 expression construct. CHO cells, which do not normally produce endothelins, produced large amounts of big ET-1 and only barely detectable amounts of mature ET-1 after transfection with the preproET-1 construct. These findings indicated that CHO cells would be suitable as host cells in all of the following expression studies.

Figure 2B:
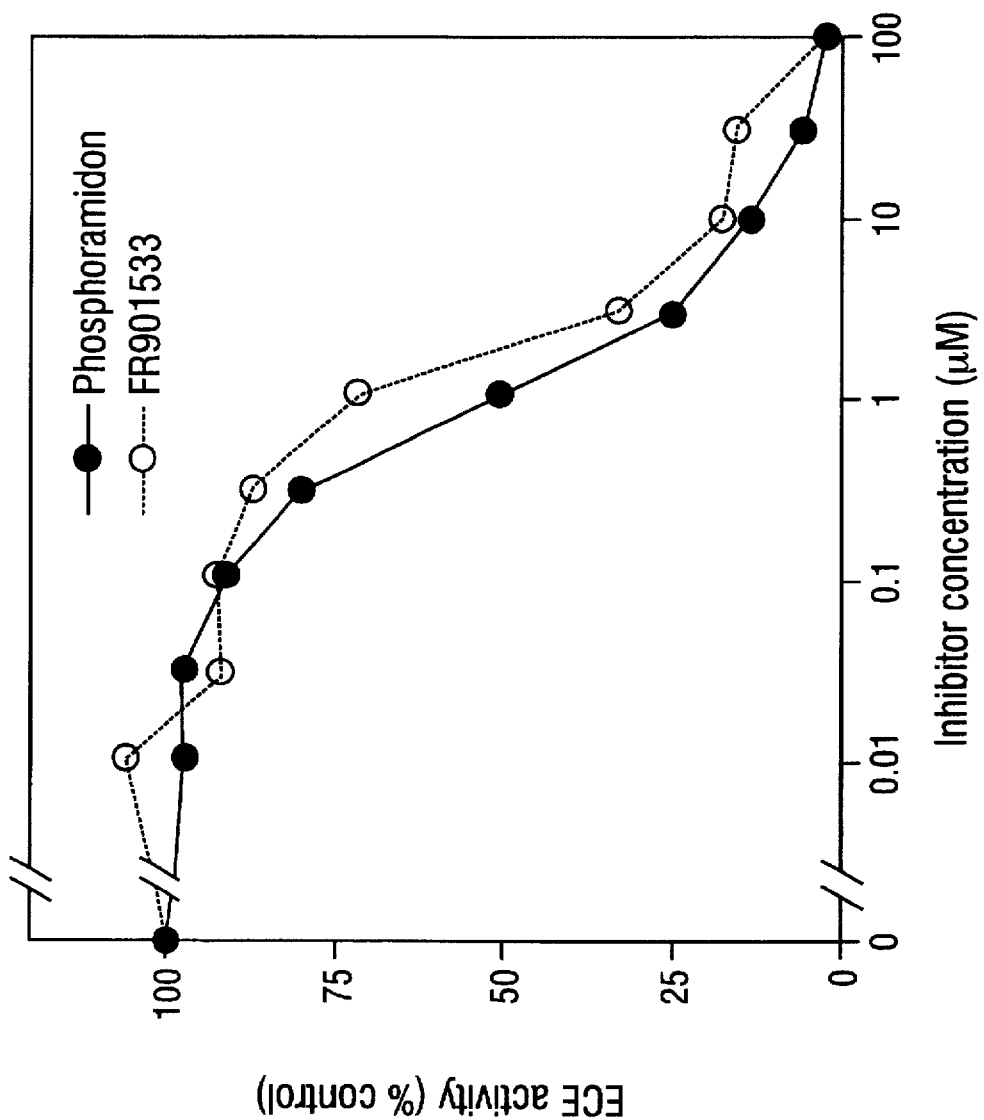
Figure 2C:
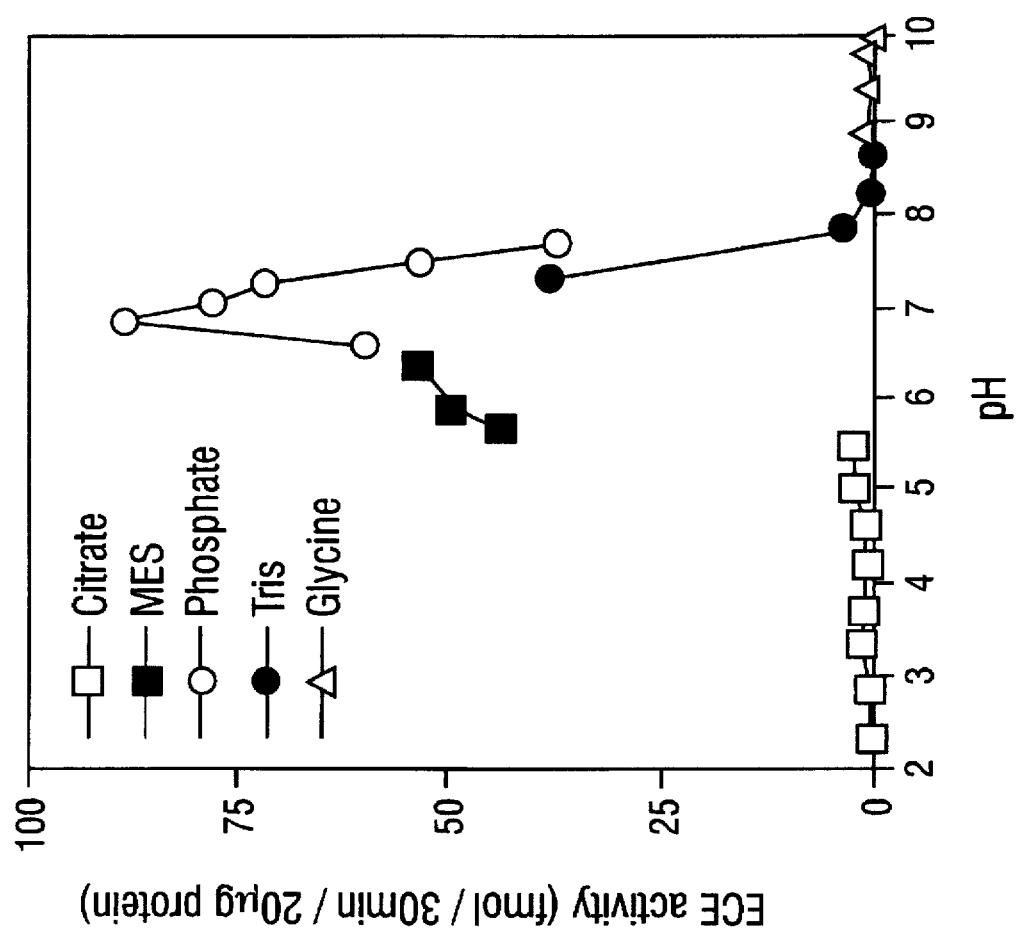
Figure 2D:
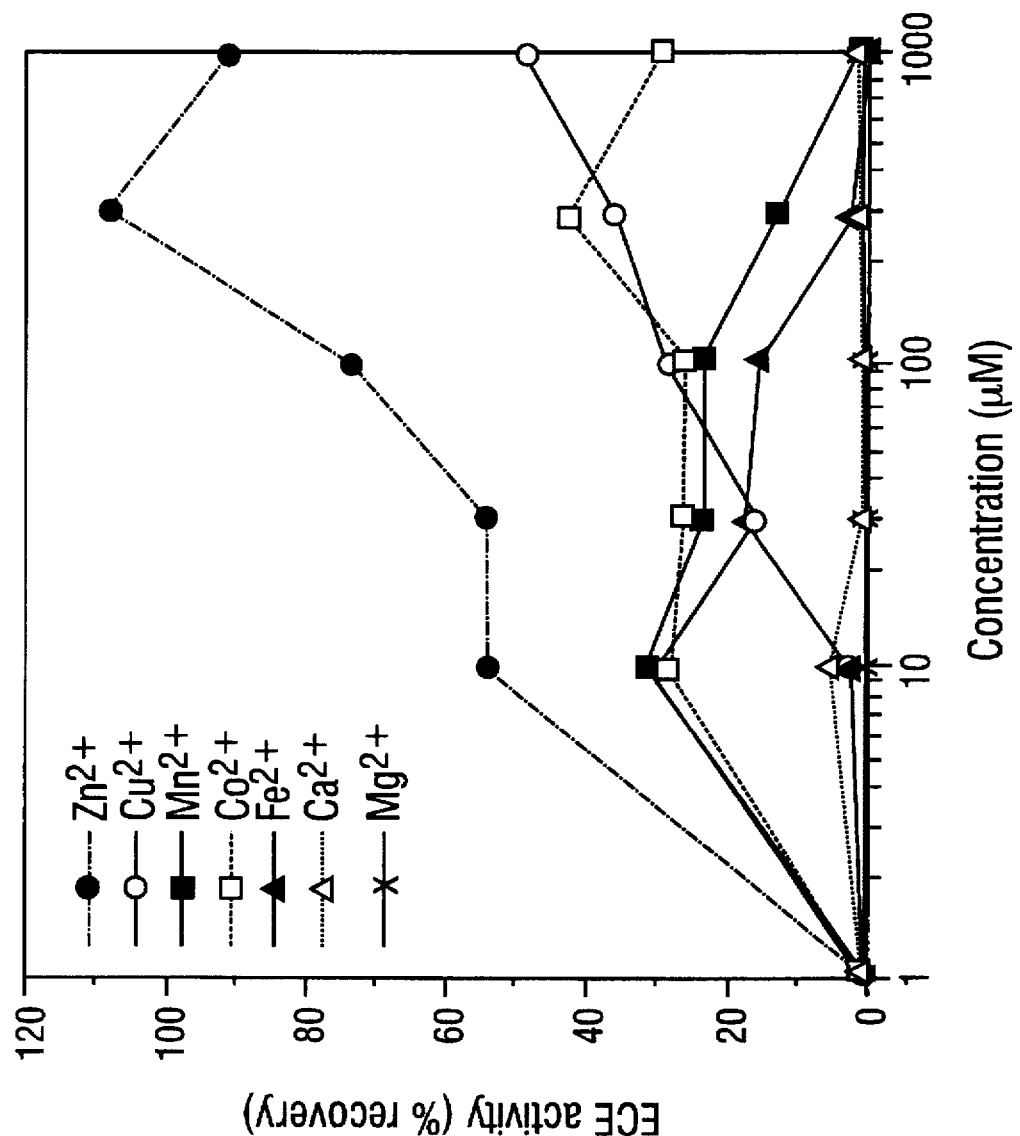
Figure 2E:
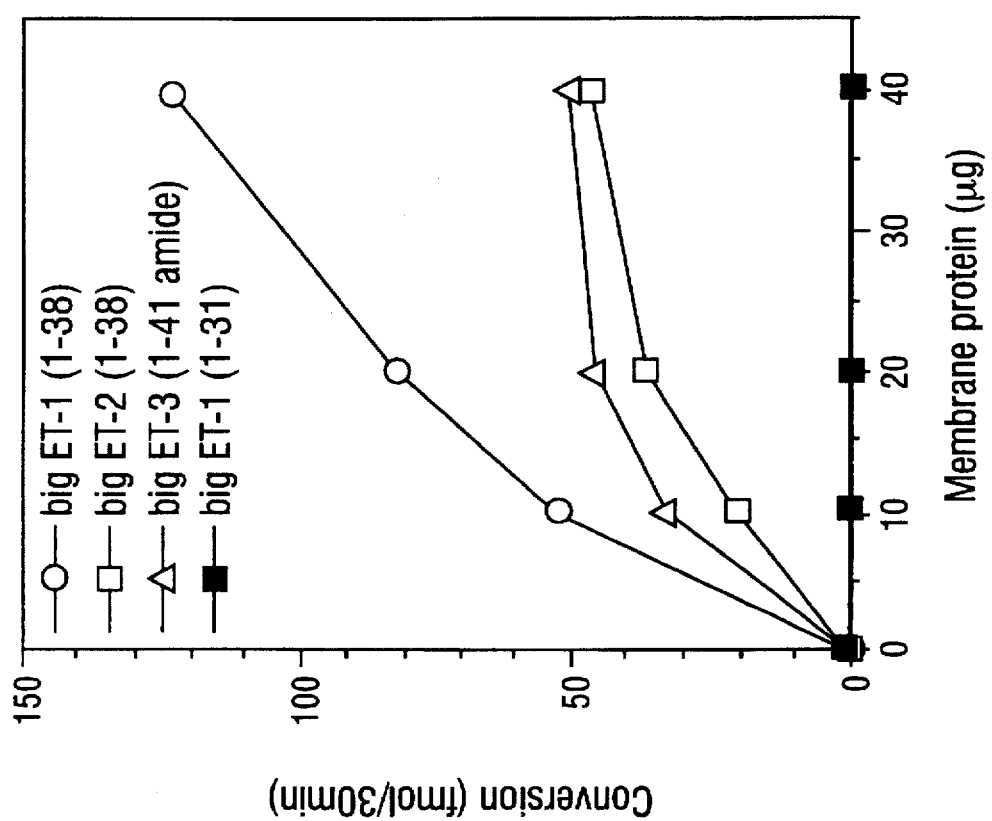

A stable transfectant cell line was obtained, CHO/ECE-1, that expresses ECE-1 mRNA from the SRα viral promoter (Sakamoto et al., 1993). Crude homogenates of CHO/ECE-1 cells efficiently converted synthetic big ET-1 into mature peptide in an in vitro assay, whereas a parallel homogenate from untransfected CHO cells exhibited no detectable ECE activity (FIG. 2A). The activity was inhibited by 100 µM phosphoramidon. Three other independent ECE-1 transfectant clones exhibited varying amounts of an ECE activity with similar properties. Virtually all ECE activity expressed in CHO/ECE-1 cells was associated with the membrane fraction, and none was detected in the cytoplasmic fraction. Culture medium conditioned with CHO/ECE-1 cells did not contain detectable levels of ECE activity, indicating that these cells did not release soluble forms of the enzyme. The ECE activity expressed in CHO/ECE-1 membranes was inhibited in vitro by EDTA, 1,10-phenanthroline, phosphoramidon, and the newly discovered specific ECE inhibitor FR901533 (Tsurumi et al., 1994) (Table 1). Phosphoramidon and FR901533 both inhibited the ECE activity in a dose dependent manner, with apparent $IC_{50}$ values of about 1 µM and 1.5 µM, respectively (FIG. 2B). The enzyme was not inhibited by thiorphan or captopril, or by inhibitors of serine, aspartic or thiol proteases (Table 1). In fact, a number of these latter inhibitors reproducibly enhanced the ECE activity, presumably by inhibiting other protease(s)

contained in the membrane preparations that may degrade the product ET-1 and/or the ECE-1 protein itself. A pH profiling study revealed a neutral optimal pH at 6.8, with a sharp pH dependence (FIG. 2C). The ECE activity was completely inhibited by 30 µM EDTA, and it was reconstituted most efficiently by $ZnCl_2$, which stimulated the enzyme activity up to 110% of the original levels at 300 µM (FIG. 2D). Cloned ECE-1 processed big ET-1 more efficiently than it did big ET-2 and big ET3 (FIG. 2E). Strikingly, ECE-1 did not generate detectable levels of mature peptide from a C-terminally truncated substrate, big ET-1(1–31), indicating the absolute requirement of the C-terminal structure of big ET-1 for enzyme recognition.

Figure 3:
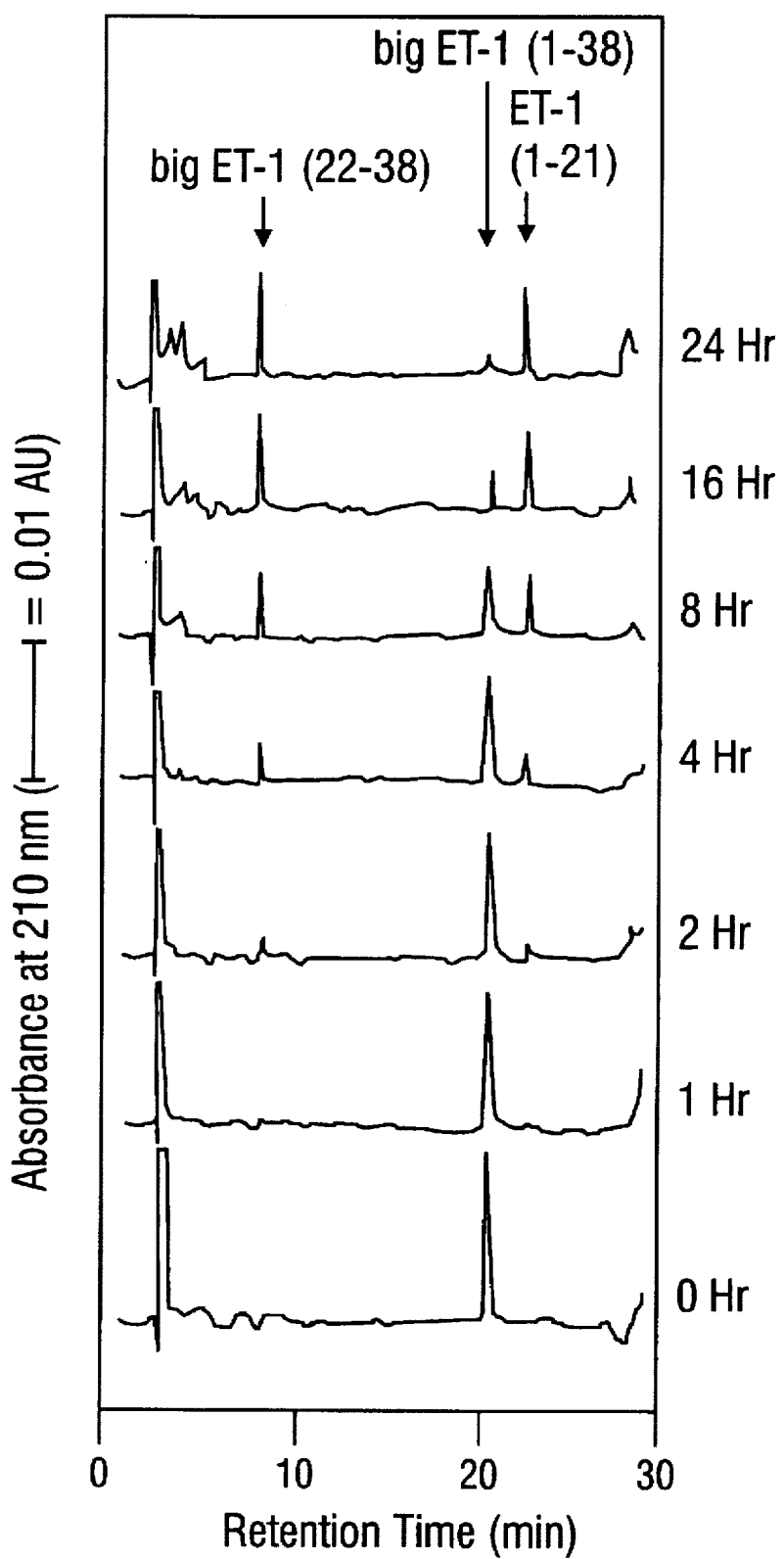

The specificity of the cleavage site in big ET-1 was examined by incubating relatively large amounts of big ET-1 with a partially purified ECE fraction from the CHO/ECE-1 membranes for prolonged periods of time, directly monitoring the cleavage by reverse-phase HPLC. Incubation of big ET-1 (5 µM) with the enzyme fraction for 24 hr resulted in a >90% conversion into two peptide products which co-eluted with mature ET-1(1-21) and big ET-1(22-38), respectively (FIG. 3). The product yield as judged by the areas under HPLC peaks was >80%. A parallel preparation from untransfected CHO cells did not appreciably cleave big ET-1. FAB-mass spectrometry of the peptide materials recovered from the two product peaks confirmed that they were ET-1(1-21) and big ET-1(22-38), with m/z values for $(M+H)^+$ of 2,493 and 1,810, respectively. These findings indicate that the cloned ECE-1 expressed in CHO cells specifically cleaves the Trp21-Val22 bond of big ET-1 without further cleaving other parts of the substrate or product.

TABLE 1

Sensitivity of ECE activity in solubilized CHO/ECE-1 membranes to protease inhibitors.

| Inhibitor (100 µM) | ECE activity (%)* |
|---|---|
| (—) | 100 |
| EDTA | 13 |
| 1,10-phenanthroline | 1 |
| Phosphoramidon | 6 |
| FR901533 | 8 |
| Thiorphan | 95 |
| Captopril | 94 |
| APMSF | 107 |
| Leupeptin | 212 |
| Chymostatin | 160 |
| Pepstatin A | 156 |
| E-64 | 115 |
| pCMS | 298 |
| NEM | 128 |

*% of ECE activity without inhibitors. Date are the means of duplicate assays from two independent experiments.

EXAMPLE 5

Functional Relevance of ECE-1 Expression in Live Transfected Cells $Ca^{2+}$ transient bioassay A CHO stable transfectant clone expressing human $ET_A$ receptors was loaded with fura-2/AM, and ET-1 induced intracellular calcium transients were monitored by a Jasco CAM-110 Intracellular Ion Analyzer as previously described (Sakamoto et al., 1993).

Results

Figure 4:
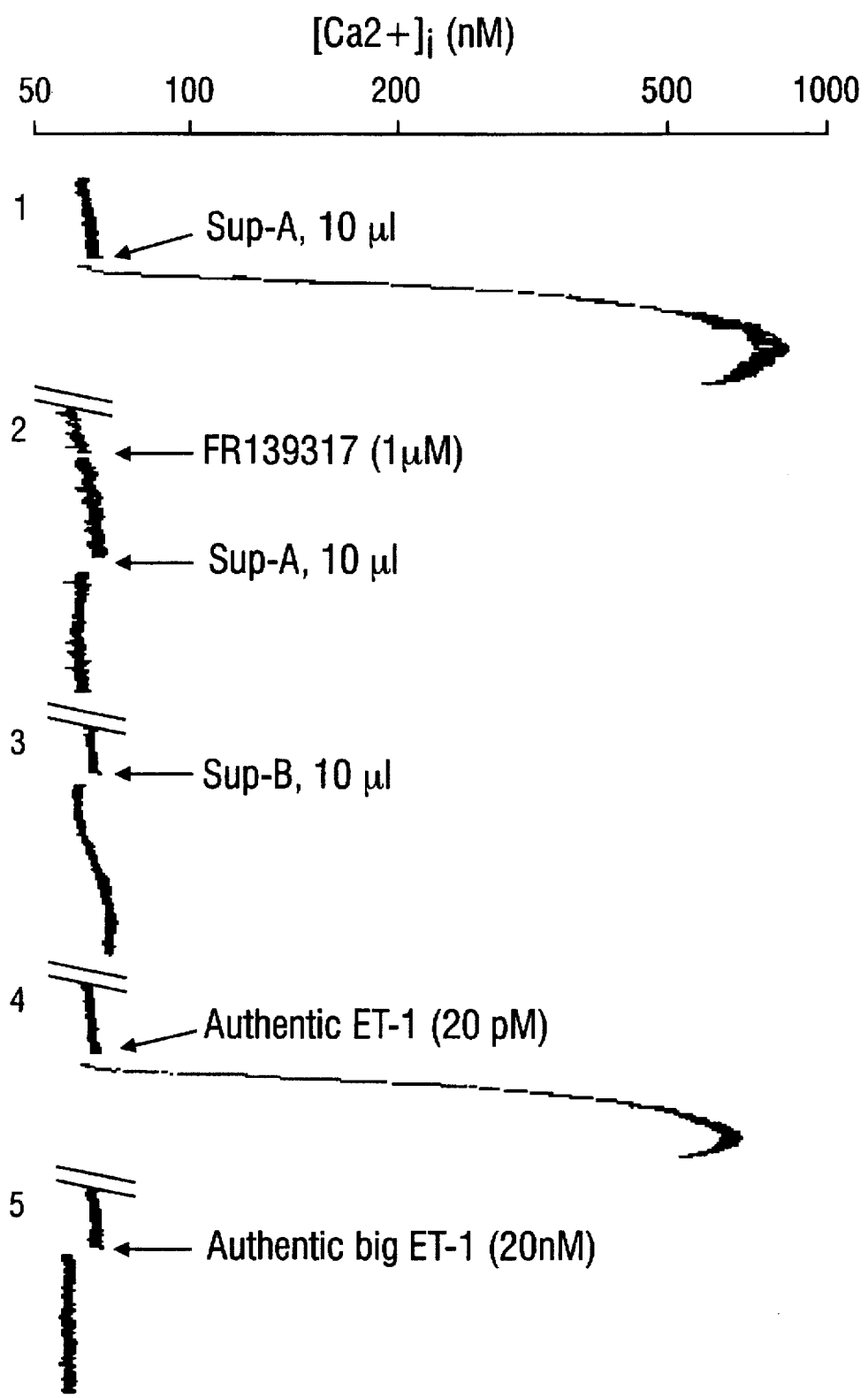

To examine whether the expressed ECE-1 can convert big ET-1 in intact cells, paired cultures of CHO/ECE-1 cells and untransfected CHO cells were transiently transfected with the preproET-1 construct. After the transient transfection, the amounts of mature and big ET-1 secreted into the medium were measured by EIA. The concentrations of big and mature ET-1 in a typical culture supernatant from the preproET-1-transfected CHO cells were 145 pM and 1.5 pM, respectively, representing only ≈1% conversion to the mature peptide. In contrast, a parallel transient transfection of CHO/ECE-1 cells produced a large amount of mature peptide (241 pM), along with a smaller amount of big ET-1 (46 pM), representing a 84% conversion. The functional authenticity of the immunoreactive mature peptide produced from the double-transfected cells was examined with a bioassay system that uses another line of CHO cells expressing human $ET_A$ receptors as reporter cells. A stable transfectant cell line was obtained by transfecting CHO cells with a human $ET_A$ receptor construct (Sakamoto et al., 1993). The cells were loaded with the $Ca^{2+}$ indicator Fura-2/AM, and directly challenged with serum-free, Phenol Red-free culture supernatants from the aforementioned double-transfection protocols. This reporter cell line exhibited a large increase in intracellular $Ca^{2+}$ in response to a final concentration of 20 pM mature ET-1 (FIG. 4, trace 4). As expected, this cell line did not respond to a 1,000-fold higher concentration of big ET-1 (trace 5). Next the supernatants from the preproET-1-transfected CHO/ECE-1 cells were added, so that the final concentration of ET-1 as measured by EIA was ≈20 pM. This produced a response of similar amplitude to that obtained with synthetic ET-1 (trace 1), and this response was completely abolished by the $ET_A$ receptor antagonist FR139317 (Sogabe et al., 1993) (trace 2). In contrast, parallel supernatants from preproET-1-transfected CHO cells did not produce a significant response (trace 3).

Taken together, these findings indicate that that ECE-1 cDNA construct confers upon transfected CHO cells the ability to secrete biologically active mature ET-1.

EXAMPLE 6

Figure 5A:
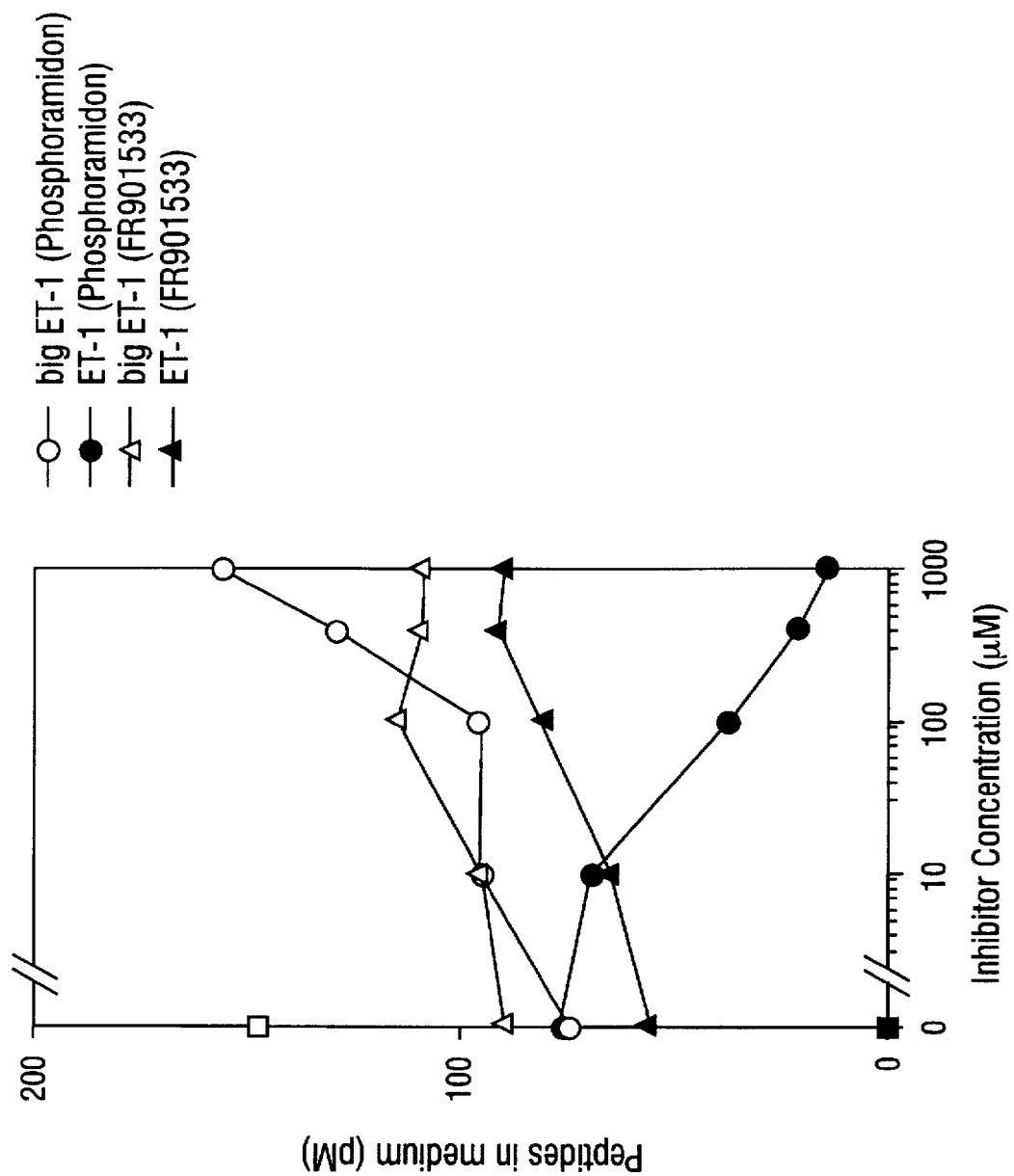

Effects of ECE Inhibitors on Production of Mature ET-1 by ECE-1-Transfected Cells This example addresses the questions, where does the conversion of endogenously synthesized big ET-1 take place, and can cells expressing ECE-1 convert exogenous big ET-1? In the double-transfected scheme described in the Example above, all CHO/ECE-1 cells express ECE-1, but only a subpopulation of the cells express preproET-1 through transient transfection. Therefore, in this case the initial source of big ET-1 is always endogenous to the CHO/ECE-1 cells. As shown in FIG. 5A, phosphoramidon added to the medium inhibited the production of mature ET-1 from the double transfected cells in a concentration dependent manner. This was accompanied by a concomitant increase of big ET-1 levels in the medium, consistent with the inhibition of its conversion into mature peptide. However, approximately 100-fold higher concentrations of phosphoramidon (apparent $IC_{50}$:≈100 µM) were required in the intact cells as compared with the inhibition of the enzyme in vitro (FIG. 5A). Moreover, FR901533, which efficiently inhibited ECE-1 in vitro with a potency similar to phosphoramidon (FIG. 2B), did not inhibit the production of ET-1 by the live cells (FIG. 5A). These findings suggest that big ET-1 is cleaved within the cells, where access to phosphoramidon and FR901533 is limited. To exclude the possibility that resistance to FR901533 was due to the degradation of FR901533 by the live cell monolayer, the concentrations of the intact compound in the medium before and after the incubation were determined by HPLC. One hundred μM of FR901533 was added nominally to the medium, and the measured concentration before and after a 72-hr culture with CHO/ECE-1 cells was determined to be 93 μM and 94 μM, respectively, indicating that the compound was not degraded by the cells.

Figure 5B:
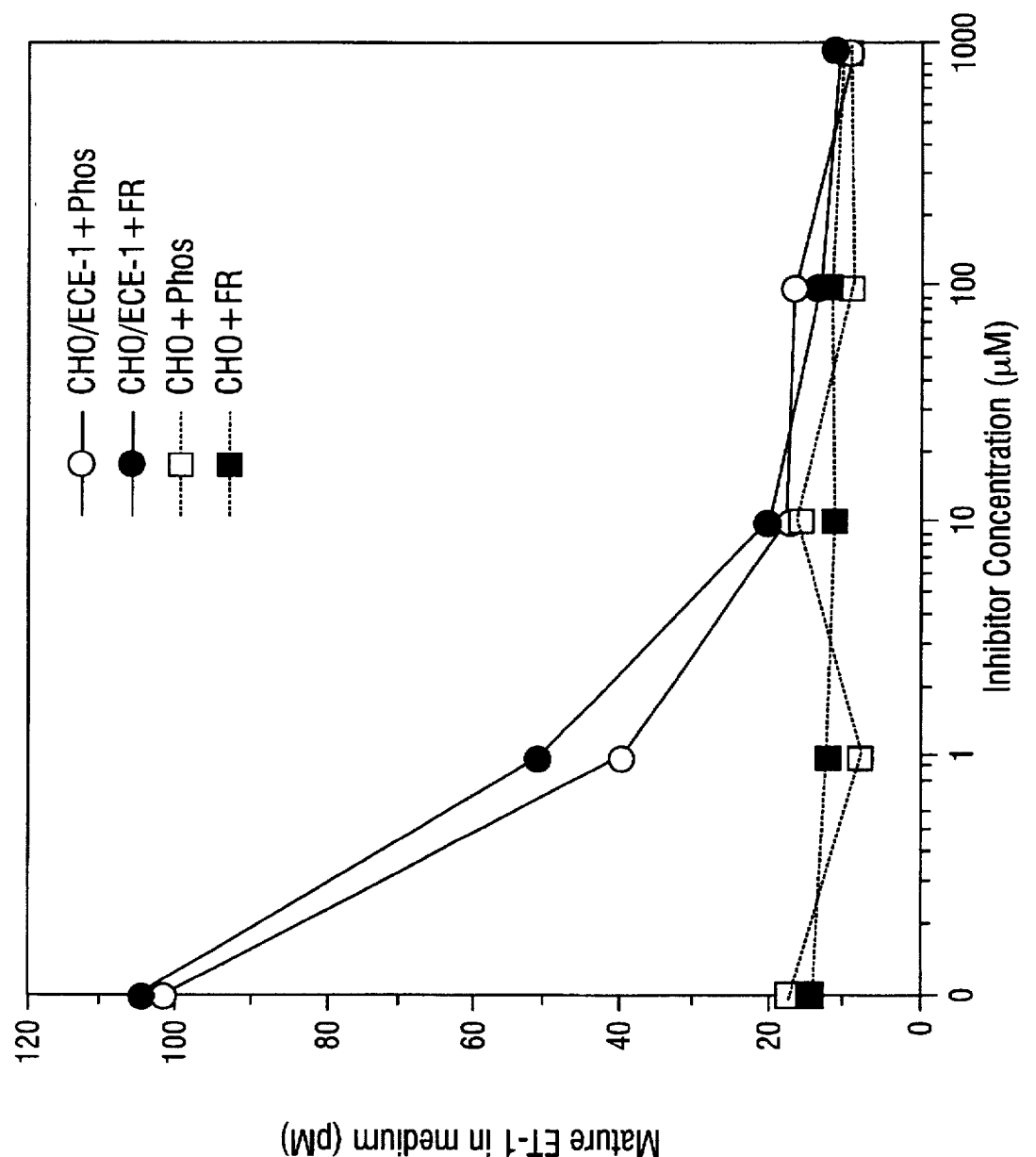

Next, the ability of CHO/ECE-1 cells to convert exogenously supplied big ET-1 was examined by co-culturing the cells with a separate CHO cell line that was stably transfected with the preproET-1 construct (CHO/preproET-1 cells). As expected, when CHO/preproET-1 cells were co-cultured with untransfected CHO cells, big ET-1 was secreted in the medium (approximately 1,500 pM) with only minimal amounts of mature peptide (FIG. 5B). In contrast, a 1:1 co-culture of CHO/preproET-1 and CHO/ECE-1 cells resulted in a significant concentration of mature ET-1 in the medium (FIG. 5B). Both phosphoramidon and FR901533 efficiently inhibited the production of ET-1 with apparent $IC_{50}$ of about 1 μM, which is similar to the $IC_{50}$ values for in vitro inhibition of ECE-1 (FIG. 2B). In addition, as compared with the conversion of endogenous big ET-1, where 50–90% conversion was consistently observed depending on experimental conditions (e.g. efficiency of transfection and timing of medium harvest), the conversion of exogenous big ET-1 was much less efficient (only up to 5–10% of big ET-1 converted).

EXAMPLE 7

Tissue distribution of ECE-1 mRNA

RNA blot analysis with the ECE-1 cDNA as probe showed that an approximately 4.7-kb ECE-1 mRNA is expressed abundantly in cultured endothelial cells from bovine coronary artery (FIG. 7, right-hand lane). In addition, a 3.1-kb mRNA is expressed in a smaller quantity. The two different sizes of the mRNA are presumably generated by alternative poly(A) addition in the 3' noncoding region (FIG. 1K). ECE-1 mRNAs are present in all of the bovine tissues examined (after longer exposures, all lanes of the blot exhibit positive signals), with exceptionally high expression in the ovary and testis followed by the adrenal gland.

In situ hybridization

Bovine tissues were collected soon after the animals were sacrificed and fixed immediately in freshly prepared 4% paraformaldehyde in PBS. Cryostat sections were cut and placed on RNase-free glass slides precoated with poly-L-lysine. Sections were permeabilized with proteinase K and hybridized with $^{35}$S-labeled RNA probes encoding bovine ECE-1 as previously described (Giaid et al., 1993). Hybridization of sections with sense probes or treatment of sections with RNase prior to hybridization with the RNA probe was used as a negative control. For generation of the RNA probe, the 0.5-kb 5' PstI/DstI fragment of bovine ECE-1 cDNA was subcloned in pBluescript vector and in vitro transcribed with T7 (anti-sense) and T3(sense) RNA polymerases.

Results

In situ hybridization confirmed the presence of ECE-1 mRNA in endothelial cells and some parenchymal cells in a variety of bovine tissues. The most striking expression was seen over vascular endothelial cells of most organs examined. A coronal section through the bovine brain cortex revealed the presence of ECE-1 mRNA over the endothelial layer of cerebral vessels. No apparent hybridization was seen over neuronal cells. In the heart, moderate to strong levels of silver grains were detected over endothelium of coronary arteries, endocardium, and over cardiac myocytes. The lungs displayed the most intense labelling among all tissues, ECE-1 mRNA being found in pulmonary epithelial cells as well as endothelial cells. The liver had less diffuse autoradiographic signals which were evident over endothelial cells of hepatic sinusoids, veins and arteries. Only scattered signals were seen over the cytoplasm of hepatocytes. In the spleen, weak to moderate levels of signals were seen over lymphocytes and endothelial cells. Adrenal glands displayed relatively strong and diffuse signals over both medulla and cortex. The signals were localized to adrenal epithelial cells and endothelial cells of sinoids and blood vessels. Examination of pancreatic tissues revealed the localization of ECE-1 mRNA to vascular endothelial cells of both arteries and capillaries, and to a lesser extent to acinar cells. Finally, moderate levels of silver grains representing ECE-1 mRNA was seen throughout the kidney, i.e. over vascular endothelial cells including those of glomerulus, and epithelial cells of tubules. Negative control experiments with a sense probe displayed only low level of background noise, confirming the specificity of the hybridization signals.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahn, K., Beningo, K., Olds, G., and Hupe, D. (1992). The endothelin-converting enzyme from human umbilical vein is a membrane-bound metalloprotease similar to that from bovine aortic endothelial cells. Proc. Natl. Acad. Sci. USA 89:8606–8610.

Arai, H., Hori, S., Aramori, I., Ohkubo, H., and Nakanishi, S. (1990). Cloning and expression of a cDNA encoding an endothelin receptor. Nature 348:730–732.

Benigni, A., Zoja, C., Corna, D., Orisio, S., Longaretti, L., Bertani, T., and Remuzzi, G. (1993). A specific endothelin subtype A receptor antagonist protects against injury in renal disease progression. Kidney Int. 44:440–444.

Bloom, I. T. M., Bentley, F. R., and Garrison, R. N. (1993). Acute cyclosporine-induced renal vasoconstriction is mediated by endothelin-1. Surgery 114:480–488.

Chen, C., and Okayama, H. (1987). High-efficiency transformation of mammalian cells by plasmid DNA. Mol. Cell. Biol. 7:2745–2752.

Clozel, M., Breu, V., Burri, K. I., Cassal, J.-M., Fischli, W., Gray, G. A., Hirth, G., Loffler, B.-M., Muller, M., Neldhart, W., and Ramuz, H. (1993). Pathophysiological role of endothelin revealed by the first orally active endothelin receptor antagonist. Nature 365:759–761.

Fernandez, J., DeMott, M., Atherton, D., and Mische, S. M. (1992). Internal protein sequence analysis: Enzymatic digestion for less than 10 μg of protein bound to polyvinylidene difluoride or nitrocellulose membranes. Anal. Biochem. 201:255–264.

Gellai, M., Jugus, M., Fletcher, T., DeWolf, R., and Nambi, P. (1994). Reversal of postischemic acute renal failure with a selective endothelin A receptor antagonist in the rat. *J. Clin. Invest.* 93:900–906.

Giaid, A., Gibson, S. J., Herrero, M. T., Gentleman, S., Leton, S., Yanagisawa, M., Masaki, T., Ibrahim, N. B. N., Roberts, G. W., Rossi, M. L., and Polak, J. M. (1991a). Topographical localisation of endothelin mRNA and peptide immunoreactivity in neurones of the human brain. *Histochemistry* 95:303–314.

Giaid, A., Polak, J. M., Gaitonde, V., Hamid, Q. A., Moscoso, G., Legon, S., Uwanogho, D., Roncalli, M., Shinmi, O., Sawamura, T., Kimural, S., Yanagisawa, M., Masaki, T., and Springall, D. R. (1991b). Distribution of endothelin-like immunoreactivity and mRNA in the developing and adult human lung. *Am. J. Respir. Cell Mol. Biol.* 4:50–58.

Giaid, A., Yanagisawa, M., Langleben, D., Michel, R. P., Levy, R., Shennib, H., Kimura, S., Masaki, T., Duguid, W. P., and Stewart, D. J. (1993). Expression of endothelin-1 in lungs of patients with pulmonary hypertension. *N. Engl. J. Med.* 328:1732–1740.

Grover, G. J., Dzwonczyk, S., and Parham, C. S. (1993). The endothelin-1 receptor antagonist BQ-123 reduces infarct size in a canine model of coronary occlusion and reperfusion. *Cardiovasc. Res.* 27:1613–1618.

Imai, T., Harata, Y., Eguchi, S., Kanno, K., Ohta, K., Emori, T., Sakamoto, A., Yanagisawa, M., Masaki, T., and Marumo, F. (1992). Concomitant expression of receptor subtype and isopeptide of endothelin by human adrenal gland. *Biochem. Biophys. Res. Comm.* 182:1115–1121.

Inoue, A., Yanagisawa, M., Kimura, S., Kasuya, Y., Miyauchi, T., Goto, K., and Masaki, T. (1989a). The human endothelin family: three structurally and pharmacologically distinct isopeptides predicted by three separate genes. *Proc. Natl. Acad. Sci. USA* 86:2863–2867.

Inoue, A., Yanagisawa, M., Takuwa, Y., Mitsui, Y., Kobayashi, M., and Masaki, T. (1989b). The human preproendothelin-1 gene. Complete nucleotide sequence and regulation of expression. *J. Biol. Chem.* 264:14954–14959.

Ito, H., Hirata, Y., Adachi, S., Tanaka, M., Tsujino, M., Koike, A., Nogami, A., Marumo, F., and Hiroe, M. (1993). Endothelin-1 is autocrine/paracrine factor in the mechanism of angiotensin II-induced hypertrophy in cultured rat cardiomyocytes. *J. Clin. Invest.* 92:398–403.

Itoh, S., Sasaki, T., Ide, K., Ishikawa, K., Nishikibe, M., and Yano, M. (1993). A novel endothelin $ET_A$ receptor antagonist, BQ-845, and its preventive effect on experimental cerebral vasospasm in dogs. *Biochem. Biophys. Res. Comm.* 195:969–975.

Jongeneel, C. V., Bouvier, J., and Bairoch, A. (1989). A unique signature identifies a family of zinc-dependent metallopeptidases. *FEBS Lett.* 242:211–214.

Kivlighn, S. D., Gabel, R. A., and Siegl, P. K. S. (1993). Effects of BQ-123 on renal function and acute cyclosporine-induced renal dysfunction. *Kidney Int.* 45:131–136.

Kurihara, Y., Kurihara, H., Suzuki, H., Kodama, T., Maemura, K., Nagai, R., Oda, H., Kuwaki, T., Cao, W., Kamada, N., Jishage, K., Ouchi, Y., Azuma, S., Toyoda, Y., Ishikawa, T., Kumada, M., and Yazaki, Y. (1994). Elevated blood pressure and craniofacial abnormalities in mice deficient in endothelin-1. *Nature* 368:703–710.

Lee, M. E., Temizer, D. H., Clifford, J. A., and Quertermous, T. (1991a). Cloning of the GABA-binding protein that regulates endothelin-1 gene expression in endothelial cells. *J. Biol. Chem.* 266:16188–16192.

Lee, S., Zambas, E. D., Marsh, W. L., and Redman, C. M. (1991b). Molecular cloning and primary structure of Kell blood group protein. *Proc. Natl. Acad. Sci. USA* 88:6353–6357.

Malfroy, B., Kuang, W. J., Seedburg, P. H., Mason, A. J., and Schofield, P. R. (1988). Molecular cloning and amino acid sequence of human enkephalinase (neutral endopeptidase). *FEBS Lett.* 229:206–210.

McMahon, E. G., Palomo, M. A., Moore, W. M., McDonald, J. R., and Stern, M. K. (1991). Phosphoramidon blocks the pressor activity of porcine big endothelin-1-(1-39) in vivo and conversion of big endothelin-1-(1-39) to endothelin-1-(1-21) in vitro. *Proc. Natl. Acad. Sci. USA* 88:703–707.

Nakajima, K., Kumagaye, S., Nishio, H., Kuroda, H., Watanabe, T., Kobayashi, Y., Tamaoki, H., Kimura, T., and Sakaibara, S. (1989). Synthesis of endothelin-1 analogues, endothelin-3, and sarafotoxin S6b: structure-activity relationships. *J. Cardiovasc. Pharmacol.* 13(Suppl. 5):S8–S12.

Nishikibe, M., Tsuchida, S., Okada, M., Fukuroda, T., Shimamoto, K., Yano, M., Ishikawa, K., and Ikemoto, F. (1993). Antihypertensive effect of a newly synthesized endothelin antagonist, BQ-123, in a genetic hypertensive model. *Life Sci.* 52:717–724.

Nishikori, K., Akiyama, H., Inagaki, Y., Ohta, H., Kashiwabara, T., Iwamatsu, A., Nomizu, M., and Morita, A. (1991). Receptor binding affinity and biological activity of c-terminal elongated forms of endothelin-1. *Neurochem. Int.* 18:535–539.

Ohlstein, E. H., Nambi, P., Douglas, S. A., Edwards, R. M., Gellai, J., Lago, A., Leber, J. D., Cousins, R. D., Gao, A., Frazee, J. S., Peishoff, C. E., Bean, J. W., Eggleston, D. S., Elshourbagy, N. A., Kumar, C., Lee, J. A., Brooks, D. P., Weinstock, J., Feuerstein, G., Poste, G., Ruffolo, R. R., Gleason, J. G., and Elliott, J. D. (1994). SB 209670, a rationally designed potent nonpeptide endothelin receptor antagonist. *Proc. Natl. Acad. Sci. USA*, in press.

Ohnaka, K., Takayanagi, R., Nishikawa, M., Haji, M., and Nawata, H. (1993). Purification and characterization of a phosphoramidon-sensitive endothelin-converting enzyme in porcine aortic endothelium. *J. Biol. Chem.* 268:26759–26766.

Okada, K., Arai, Y., Hata, M., Matsuyama, K., and Yano, M. (1993). Big endothelin-1 structure important for specific processing by endothelin-converting enzyme of bovine endothelial cells. *Eur. J. Biochem.* 218:493–498.

Okada, K., Miyazaki, Y., Takada, J., Matsuyama, K., Yamaki, T., and Yano, M. (1990). Conversion of big endothelin-1 by membrane-bound metalloendopeptidase in cultured bovine endothelial cells. *Biochem. Biophys. Res. Comm.* 171:1192–1198.

Opgenorth, T. J., Wu-Wong, J. R., and Shiosaki, K. (1992). Endothelin-converting enzymes. *FASEB J.* 6:2653–2659.

Roques, B. P., Noble, F., Dauge, V., Fournie-Zaluski, M.-C., and Beaumont, A. (1993). Neutral endopeptidase 24.11: Structure, inhibition, and experimental and clinical pharmacology. *Pharmacol. Rev.* 45:87–146.

Rosolowsky, L. J., and Campbell, W. B. (1994). Endothelial cells stimulate aldosterone release from bovine adrenal zona glomerulosa cells. *Am. J. Physiol.* 266:E107–E17.

Sakatomo, A., Yanagisawa, M., Sawamura, T., Enoki, T., Ohtani, T., Sakurai, T., Nakao, K., Toyo-oka, T., and Masaki, T. (1993). Distinct subdomains of human endothelin receptors determine their selectivity to $ET_A$-selective antagonist and $ET_B$-selective agonist. *J. Biol. Chem.* 268:8547–8553.

Sakurai, T., Yanigisawa, M., Takuwa, Y., Miyazaki, H., Kimura, S., Goto, K., and Masaki, T. (1990). Cloning of a cDNA encoding a non-isopeptide-selective subtype of the endothelin receptor. *Nature* 348:732–735.

Sawamura, T., Kasuya, Y., Matshushita, Y., Suzuki, N., Shinmi, O., Kishi, N., Sugita, Y., Yanagisawa, M., Goto, K., Masaki, T., and Kimura, S. (1991). Phosphoramidon inhibits the intracellular conversion of big endothelin-1 to endothelin-1 in cultured endothelial cells. *Biochem. Biophys. Res. Comm.* 174:779–784.

Seidah, N. G., Day, R., Marcinkiewicz, M., and Chretien, M. (1993). Mammalian paired basic amino acid convertases of prohormones and proproteins. *Ann. New York Acad. Sci.* 680:135–146.

Simonson, M. S., and Dunn, M. J. (1991). Endothelins: a family of regulatory peptides. *Hypertension* 17:856–863.

Sogabe, K., Nirei, H., Shoubo, M., Nomoto, A., Ao, S., Notsu, Y., and Ono, T. (1993). Pharmacological profile of FR139317, a novel, potent endothelin ETA receptor antagonist. *J. Pharmacol. Exp. Ther.* 264:1040–1046.

Suzuki, N., Matsumoto, H., Kitada, C., Kimura, S., Miyauchi, T., and Fujino, M. (1990). A sandwich-type enzyme immunoassay to detect immunoreactive big-endothelin-1 in plasma. *J. Immunol. Meth.* 127:1650170.

Suzuki, N., Matsumoto, H., Kitada, C., Masaki, T., and Fujino, M. (1989). A sensitive sandwich-enzyme immunoassay for human endothelin. *J. Immunol. Meth.* 118:245–250.

Takahashi, M., Matsushita, Y., Iijima, Y., and Tanzawa, K. (1993). Purification and characterization of endothelin-converting enzyme from rat lung. *J. Biol. Chem.* 268:21395–21398.

Tsurumi, Y., Ohhata, N., Iwamoto, T., Shigematsu, N., Sakamoto, K., Nishikawa, M., Kiyoto, S., and Okuhara, M. (1994). WS79089A, B and C, new endothelin converting enzyme inhibitors isolated from *Streptosproangium roseum* NO>89089. *J. Antibiotics* 47:667–678.

Turner, A. J. (1993). Endothelin-converting enzymes and other families of metalloendopeptidases. *Biochem. Soc. Trans.* 21:596–701.

Ujiie, K., Tarada, Y., Nonoguchi, H., Shinohara, M., Tomita, K., and Marumo, F. (1992). Messenger RNA expression and synthesis of endothelin-1 along rat nephron segments. *J. Clin. Invest.* 90:1043–1048.

Vane, J. R., and Botting, R. M. (1992). Secretory functions of the vascular endothelium. *J. Physiol. Pharmacol.* 43:195–207.

Vijayaraghavan, J., Scicli, A. G., Carretero, O. A., Slaughter, C., Moomaw, C., and Hersh, L. B. (1990). The hydrolysis of endothelins by neutral endopeptidase 24.11 (enkephalinase). *J. Biol. Chem.* 265:14150–14155.

Waxman, L., Doshi, K. P., Gaul, S. L., Wang, S., Rodney, A. B., and Stern, A. M. (1993). Identification and characterization of endothelin converting activity from EAHY 926 cells: Evidence for the physiologically relevant human enzymes. *Arch. Biochem. Biophy.* 308:240–253.

Yanagisawa, M. (1994). The endothelin system: A new target for therapeutic intervention. *Circulation* 89:1320–1322.

Yanagisawa, M., Kurihara, H., Kimura, S., Tomobe, Y., Kobayashi, M., Mitsui, Y., Yazaki, Y., Goto, K., and Masaki, T. (1988). A novel potent vasoconstrictor peptide produced by vascular endothelial cells. *Nature* 332:411–415.

Yokokawa, K., Tahara, H., Kohno, M., Murakawa, K., Yasunari, K., Nakagawa, K., Hamada, T., Otani, S., Yanagisawa, M., and Takeda, T. (1991). Hypertension associated with endothelin-secreting malignant hemangioendothelioma. *Ann. Intern. Med.* 114:213–215.

---

What is claimed is:

1. A method of screening substances as effectors of endothelin converting enzyme comprising the following steps:
   (a) obtaining a candidate substance;
   (b) obtaining a recombinant endothelin converting enzyme, wherein the enzyme comprises an amino acid sequence in accordance with SEQ ID NO:2;
   (c) contacting said endothelin converting enzyme with big endothelin under conditions effective to convert big endothelin to endothelin in the presence of said candidate substance;
   (d) measuring the concentration of endothelin produced; and
   (e) comparing the concentration of endothelin produced in the presence of said candidate substance to the concentration of endothelin produced under a control having identical conditions but in the absence of said candidate substance;
wherein a decrease or increase in the concentration of endothelin produced in the presence of said candidate substance compared to the control would indicate an effector of endothelin converting enzyme.

2. The method of claim 1, wherein said recombinant endothelin converting enzyme is encoded by a recombinant nucleic acid segment comprising a nucleic acid sequence in accordance with SEQ ID NO:1.

3. The method of claim 1 wherein said recombinant endothelin converting enzyme is produced in a cell and said cells are contacted with big endothelin and said candidate substance.

4. The method of claim 3, wherein said cells are CHO cells.

5. The method of claim 2, wherein said recombinant nucleic acid segment is contained in an expression vector capable of expressing endothelin converting enzyme polypeptide upon introduction into a cell.

6. The method of claim 3, wherein said contacting said cells with big endothelin comprises expressing preproET-1 in said cells.

\* \* \* \* \*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 2889 base pairs
      ( B ) TYPE: nucleic acid
      ( C ) STRANDEDNESS: single
      ( D ) TOPOLOGY: linear ( i i ) MOLECULE TYPE: DNA ( i x ) FEATURE:
      ( A ) NAME/KEY: CDS
      ( B ) LOCATION: 118..2391

( x i ) SEQUENCE DESCRIPTION: SEQ ID NO:1:

```
AGCGCGGCTG  GGCTGGGCTG  CTTGACTCCG  AGCTGCTGAG  CAGGGTGGCC  GTTCCTCTCC   60

TGGATTAGGA  CGGTTCCGTG  GGAACCAGAC  CACCCCTGAG  ACGGGAGGGC  GGCCCTG     117

ATG  TCT  CCC  CGG  GGC  CAG  GAT  CTG  CTG  CGG  AGC  CCC  CTC  CTC  CTG  GGC   165
Met  Ser  Pro  Arg  Gly  Gln  Asp  Leu  Leu  Arg  Ser  Pro  Leu  Leu  Leu  Gly
 1             5                       10                      15

AGC  GAG  GCC  CCT  GGG  CTC  ACG  TCC  TCC  CCG  TTC  CGC  CTG  CCT  CCT  TCC   213
Ser  Glu  Ala  Pro  Gly  Leu  Thr  Ser  Ser  Pro  Phe  Arg  Leu  Pro  Pro  Ser
         20                      25                      30

CTG  CAG  GTG  AAC  TTC  CGA  GGC  CCC  CGG  AAC  GGC  CAG  AGA  TGC  TGG  GCC   261
```

|  |  |  |  |  |  |  |  |  |  |  |  |  |  |  |  |
|---|---|---|---|---|---|---|---|---|---|---|---|---|---|---|---|
| Leu | Gln | Val 35 | Asn | Phe | Arg | Gly | Pro 40 | Arg | Asn | Gly | Gln | Arg 45 | Cys | Trp | Ala |

| GCC | AGG | ACC | CCG | GTG | GAG | AAG | CGG | CTG | GTG | GTG | CTG | GTG | GCG | CTC | CTG | 309 |
|---|---|---|---|---|---|---|---|---|---|---|---|---|---|---|---|---|
| Ala | Arg 50 | Thr | Pro | Val | Glu | Lys 55 | Arg | Leu | Val | Val | Leu 60 | Val | Ala | Leu | Leu | |

| GCG | GCG | GCA | TTG | GTG | GCC | TGT | TTG | GCA | GTA | CTG | GGC | ATC | CAA | TAC | CAG | 357 |
|---|---|---|---|---|---|---|---|---|---|---|---|---|---|---|---|---|
| Ala 65 | Ala | Ala | Leu | Val | Ala 70 | Cys | Leu | Ala | Val | Leu 75 | Gly | Ile | Gln | Tyr | Gln 80 | |

| ACA | AGA | ACG | CCC | TCG | GTG | TGC | CTA | AGT | GAG | GGC | TGC | ATC | TCG | GTG | ACC | 405 |
|---|---|---|---|---|---|---|---|---|---|---|---|---|---|---|---|---|
| Thr | Arg | Thr | Pro | Ser 85 | Val | Cys | Leu | Ser | Glu 90 | Gly | Cys | Ile | Ser | Val 95 | Thr | |

| AGC | TCC | ATC | TTG | AGT | TCC | ATG | GAC | CCC | ACG | GTG | GAC | CCC | TGC | CAG | GAC | 453 |
|---|---|---|---|---|---|---|---|---|---|---|---|---|---|---|---|---|
| Ser | Ser | Ile | Leu 100 | Ser | Ser | Met | Asp | Pro 105 | Thr | Val | Asp | Pro | Cys 110 | Gln | Asp | |

| TTC | TTC | ACC | TAT | GCC | TGT | GGC | GGC | TGG | ATC | AAA | GCC | AAC | CCC | GTG | CCG | 501 |
|---|---|---|---|---|---|---|---|---|---|---|---|---|---|---|---|---|
| Phe | Phe | Thr | Tyr 115 | Ala | Cys | Gly | Gly | Trp 120 | Ile | Lys | Ala | Asn | Pro 125 | Val | Pro | |

| GAT | GGC | CAC | TCG | CGC | TGG | GGG | ACC | TTC | AGC | AAC | CTC | TGG | GAA | CAC | AAC | 549 |
|---|---|---|---|---|---|---|---|---|---|---|---|---|---|---|---|---|
| Asp | Gly | His | Ser 130 | Arg | Trp | Gly | Thr | Phe 135 | Ser | Asn | Leu | Trp | Glu 140 | His | Asn | |

| CAA | GCC | ATC | ATC | AAG | CAC | CTC | CTT | GAA | AAC | TCC | ACG | GCC | AGC | GTG | AGC | 597 |
|---|---|---|---|---|---|---|---|---|---|---|---|---|---|---|---|---|
| Gln 145 | Ala | Ile | Ile | Lys | His 150 | Leu | Leu | Glu | Asn | Ser 155 | Thr | Ala | Ser | Val | Ser 160 | |

| GAG | GCA | GAG | AGG | AAG | GCC | CAG | GTG | TAC | TAC | CGA | GCC | TGC | ATG | AAC | GAA | 645 |
|---|---|---|---|---|---|---|---|---|---|---|---|---|---|---|---|---|
| Glu | Ala | Glu | Arg | Lys 165 | Ala | Gln | Val | Tyr | Tyr 170 | Arg | Ala | Cys | Met | Asn 175 | Glu | |

| ACC | AGG | ATT | GAG | GAG | CTC | AAG | GCC | AAA | CCC | CTG | ATG | GAG | CTC | ATT | GAG | 693 |
|---|---|---|---|---|---|---|---|---|---|---|---|---|---|---|---|---|
| Thr | Arg | Ile | Glu 180 | Glu | Leu | Lys | Ala | Lys 185 | Pro | Leu | Met | Glu | Leu 190 | Ile | Glu | |

| AAG | CTC | GGC | GGC | TGG | AAC | ATC | ACG | GGG | CCC | TGG | GAC | AAG | GAC | AAC | TTC | 741 |
|---|---|---|---|---|---|---|---|---|---|---|---|---|---|---|---|---|
| Lys | Leu | Gly 195 | Gly | Trp | Asn | Ile | Thr 200 | Gly | Pro | Trp | Asp | Lys 205 | Asp | Asn | Phe | |

| CAG | GAC | ACC | CTG | CAG | GTG | GTC | ACA | TCC | CAC | TAC | CAC | ACC | TCC | CCC | TTC | 789 |
|---|---|---|---|---|---|---|---|---|---|---|---|---|---|---|---|---|
| Gln | Asp | Thr 210 | Leu | Gln | Val | Val | Thr 215 | Ser | His | Tyr | His | Thr 220 | Ser | Pro | Phe | |

| TTC | TCC | GTC | TAC | GTC | AGT | GCC | GAC | TCC | AAG | AAT | TCC | AAC | AGC | AAC | GTG | 837 |
|---|---|---|---|---|---|---|---|---|---|---|---|---|---|---|---|---|
| Phe 225 | Ser | Val | Tyr | Val | Ser 230 | Ala | Asp | Ser | Lys | Asn 235 | Ser | Asn | Ser | Asn | Val 240 | |

| ATC | CAA | GTG | GAC | CAG | TCT | GGC | CTG | GGC | TTA | CCC | TCA | AGA | GAT | TAT | TAC | 885 |
|---|---|---|---|---|---|---|---|---|---|---|---|---|---|---|---|---|
| Ile | Gln | Val | Asp | Gln 245 | Ser | Gly | Leu | Gly | Leu 250 | Pro | Ser | Arg | Asp | Tyr 255 | Tyr | |

| CTG | AAC | AAA | ACC | GAG | AAT | GAG | AAG | GTG | CTG | ACG | GGA | TAC | CTG | AAC | TAC | 933 |
|---|---|---|---|---|---|---|---|---|---|---|---|---|---|---|---|---|
| Leu | Asn | Lys | Thr 260 | Glu | Asn | Glu | Lys | Val 265 | Leu | Thr | Gly | Tyr | Leu 270 | Asn | Tyr | |

| ATG | GTC | CAG | CTG | GGG | AAG | CTG | CTG | GGA | GGA | GGG | GCC | GAG | GAC | ACC | ATC | 981 |
|---|---|---|---|---|---|---|---|---|---|---|---|---|---|---|---|---|
| Met | Val | Gln | Leu 275 | Gly | Lys | Leu | Leu | Gly 280 | Gly | Gly | Ala | Glu | Asp 285 | Thr | Ile | |

| CGG | CCC | CAG | ATG | CAG | CAG | ATC | CTG | GAC | TTT | GAG | ACG | GCG | CTG | GCC | AAC | 1029 |
|---|---|---|---|---|---|---|---|---|---|---|---|---|---|---|---|---|
| Arg | Pro 290 | Gln | Met | Gln | Gln | Ile 295 | Leu | Asp | Phe | Glu | Thr 300 | Ala | Leu | Ala | Asn | |

| ATC | ACC | ATC | CCC | CAG | GAG | AAG | CGC | CGG | GAC | GAG | GAA | CTC | ATC | TAC | CAC | 1077 |
|---|---|---|---|---|---|---|---|---|---|---|---|---|---|---|---|---|
| Ile 305 | Thr | Ile | Pro | Gln | Glu 310 | Lys | Arg | Arg | Asp | Glu 315 | Glu | Leu | Ile | Tyr | His 320 | |

| AAA | GTG | ACG | GCG | GCT | GAG | TTG | CAG | ACC | TTG | GCG | CCC | GCC | ATC | AAC | TGG | 1125 |
|---|---|---|---|---|---|---|---|---|---|---|---|---|---|---|---|---|
| Lys | Val | Thr | Ala | Ala 325 | Glu | Leu | Gln | Thr | Leu 330 | Ala | Pro | Ala | Ile | Asn 335 | Trp | |

| CTG | CCC | TTC | CTC | AAC | ACC | ATC | TTC | TAC | CCC | GTG | GAG | ATC | AAT | GAA | TCA | 1173 |
|---|---|---|---|---|---|---|---|---|---|---|---|---|---|---|---|---|
| Leu | Pro | Phe | Leu | Asn 340 | Thr | Ile | Phe | Tyr | Pro 345 | Val | Glu | Ile | Asn | Glu 350 | Ser | |

| GAG | CCT | ATT | GTC | ATC | TAC | GAC | AAA | GAA | TAC | CTG | AGC | AAG | GTC | TCC | ACC | 1221 |

| | | | | | | | | | | | | | | |
|---|---|---|---|---|---|---|---|---|---|---|---|---|---|---|
| Glu | Pro | Ile 355 | Val | Ile | Tyr | Asp | Lys 360 | Glu | Tyr | Leu | Ser | Lys 365 | Val | Ser | Thr |

| | | | | | | | | | | | | | | | |
|---|---|---|---|---|---|---|---|---|---|---|---|---|---|---|---|
| CTC | ATC | AAC | AGC | ACA | GAC | AAA | TGC | CTG | CTG | AAC | AAC | TAC | ATG | ATC | TGG | 1269 |
| Leu | Ile 370 | Asn | Ser | Thr | Asp | Lys 375 | Cys | Leu | Leu | Asn | Asn 380 | Tyr | Met | Ile | Trp |

| AAC | CTG | GTA | CGG | AAG | ACG | AGC | TCC | TTC | CTC | GAT | CAG | CGC | TTC | CAG | GAC | 1317 |
|---|---|---|---|---|---|---|---|---|---|---|---|---|---|---|---|---|
| Asn 385 | Leu | Val | Arg | Lys 390 | Thr | Ser | Ser | Phe | Leu 395 | Asp | Gln | Arg | Phe | Gln | Asp 400 |

| GCC | GAC | GAG | AAG | TTC | ATG | GAA | GTC | ATG | TAT | GGG | ACC | AAG | AAG | ACG | TGT | 1365 |
|---|---|---|---|---|---|---|---|---|---|---|---|---|---|---|---|---|
| Ala | Asp | Glu | Lys | Phe 405 | Met | Glu | Val | Met | Tyr 410 | Gly | Thr | Lys | Lys | Thr 415 | Cys |

| CTT | CCC | CGC | TGG | AAG | TTT | TGT | GTG | AGT | GAT | ACA | GAG | AAC | ACC | TTG | GGC | 1413 |
|---|---|---|---|---|---|---|---|---|---|---|---|---|---|---|---|---|
| Leu | Pro | Arg | Trp 420 | Lys | Phe | Cys | Val | Ser 425 | Asp | Thr | Glu | Asn | Thr 430 | Leu | Gly |

| TTC | GCC | CTG | GGC | CCC | ATG | TTC | GTC | AAA | GCG | ACC | TTC | GCT | GAG | GAC | AGC | 1461 |
|---|---|---|---|---|---|---|---|---|---|---|---|---|---|---|---|---|
| Phe | Ala | Leu 435 | Gly | Pro | Met | Phe | Val 440 | Lys | Ala | Thr | Phe | Ala 445 | Glu | Asp | Ser |

| AAG | AAC | ATA | GCC | AGC | GAG | ATC | ATC | CTG | GAG | ATC | AAG | AAG | GCG | TTT | GAA | 1509 |
|---|---|---|---|---|---|---|---|---|---|---|---|---|---|---|---|---|
| Lys | Asn 450 | Ile | Ala | Ser | Glu | Ile 455 | Ile | Leu | Glu | Ile | Lys 460 | Lys | Ala | Phe | Glu |

| GAG | AGC | CTG | AGC | ACC | CTG | AAG | TGG | ATG | GAT | GAA | GAT | ACT | CGG | AAA | TCG | 1557 |
|---|---|---|---|---|---|---|---|---|---|---|---|---|---|---|---|---|
| Glu 465 | Ser | Leu | Ser | Thr | Leu 470 | Lys | Trp | Met | Asp | Glu 475 | Asp | Thr | Arg | Lys | Ser 480 |

| GCC | AAG | GAA | AAG | GCG | GAC | GCG | ATC | TAC | AAC | ATG | ATA | GGC | TAC | CCC | AAC | 1605 |
|---|---|---|---|---|---|---|---|---|---|---|---|---|---|---|---|---|
| Ala | Lys | Glu | Lys | Ala 485 | Asp | Ala | Ile | Tyr | Asn 490 | Met | Ile | Gly | Tyr | Pro 495 | Asn |

| TTT | ATC | ATG | GAC | CCC | AAG | GAG | CTG | GAC | AAA | GTG | TTC | AAT | GAC | TAC | ACC | 1653 |
|---|---|---|---|---|---|---|---|---|---|---|---|---|---|---|---|---|
| Phe | Ile | Met | Asp 500 | Pro | Lys | Glu | Leu | Asp 505 | Lys | Val | Phe | Asn | Asp 510 | Tyr | Thr |

| GCT | GTG | CCA | GAC | CTC | TAC | TTC | GAG | AAC | GCC | ATG | CGG | TTT | TTC | AAC | TTC | 1701 |
|---|---|---|---|---|---|---|---|---|---|---|---|---|---|---|---|---|
| Ala | Val | Pro 515 | Asp | Leu | Tyr | Phe | Glu 520 | Asn | Ala | Met | Arg | Phe 525 | Phe | Asn | Phe |

| TCC | TGG | AGG | GTC | ACT | GCC | GAC | CAG | CTC | CGG | AAA | GCG | CCC | AAC | AGA | GAT | 1749 |
|---|---|---|---|---|---|---|---|---|---|---|---|---|---|---|---|---|
| Ser | Trp 530 | Arg | Val | Thr | Ala | Asp 535 | Gln | Leu | Arg | Lys | Ala 540 | Pro | Asn | Arg | Asp |

| CAG | TGG | AGC | ATG | ACC | CCG | CCC | ATG | GTG | AAC | GCC | TAC | TAC | TCG | CCC | ACC | 1797 |
|---|---|---|---|---|---|---|---|---|---|---|---|---|---|---|---|---|
| Gln 545 | Trp | Ser | Met | Thr | Pro 550 | Pro | Met | Val | Asn | Ala 555 | Tyr | Tyr | Ser | Pro | Thr 560 |

| AAG | AAC | GAG | ATC | GTG | TTT | CCG | GCC | GGA | ATC | CTG | CAG | GCG | CCA | TTC | TAC | 1845 |
|---|---|---|---|---|---|---|---|---|---|---|---|---|---|---|---|---|
| Lys | Asn | Glu | Ile | Val 565 | Phe | Pro | Ala | Gly | Ile 570 | Leu | Gln | Ala | Pro | Phe 575 | Tyr |

| ACC | CGC | TCT | TCA | CCC | AAT | GCC | TTA | AAC | TTC | GGC | GGC | ATC | GGC | GTC | GTC | 1893 |
|---|---|---|---|---|---|---|---|---|---|---|---|---|---|---|---|---|
| Thr | Arg | Ser | Ser 580 | Pro | Asn | Ala | Leu | Asn 585 | Phe | Gly | Gly | Ile | Gly 590 | Val | Val |

| GTG | GGC | CAC | GAG | CTG | ACT | CAT | GCT | TTT | GAT | GAT | CAA | GGC | CGA | GAG | TAC | 1941 |
|---|---|---|---|---|---|---|---|---|---|---|---|---|---|---|---|---|
| Val | Gly | His 595 | Glu | Leu | Thr | His | Ala 600 | Phe | Asp | Asp | Gln | Gly 605 | Arg | Glu | Tyr |

| GAC | AAG | GAT | GGG | AAC | CTC | CGG | CCC | TGG | TGG | AAG | AAC | TCG | TCC | GTG | GAG | 1989 |
|---|---|---|---|---|---|---|---|---|---|---|---|---|---|---|---|---|
| Asp | Lys | Asp 610 | Gly | Asn | Leu | Arg | Pro 615 | Trp | Trp | Lys | Asn | Ser 620 | Ser | Val | Glu |

| GCG | TTC | AAG | CAG | CAG | ACC | GCG | TGC | ATG | GTG | GAG | CAG | TAC | GGC | AAC | TAT | 2037 |
|---|---|---|---|---|---|---|---|---|---|---|---|---|---|---|---|---|
| Ala | Phe | Lys | Gln | Gln 625 | Thr | Ala | Cys | Met | Val 630 | Glu | Gln | Tyr | Gly | Asn 635 | Tyr 640 |

| AGC | GTG | AAC | GGG | GAG | CCG | GTG | AAC | GGC | CGG | CAC | ACC | CTC | GGC | GAA | AAC | 2085 |
|---|---|---|---|---|---|---|---|---|---|---|---|---|---|---|---|---|
| Ser | Val | Asn | Gly | Glu 645 | Pro | Val | Asn | Gly | Arg 650 | His | Thr | Leu | Gly | Glu 655 | Asn |

| ATC | GCC | GAC | AAC | GGG | GGC | CTC | AAG | GCG | GCC | TAT | CGG | GCC | TAC | CAG | AAC | 2133 |
|---|---|---|---|---|---|---|---|---|---|---|---|---|---|---|---|---|
| Ile | Ala | Asp | Asn 660 | Gly | Gly | Leu | Lys | Ala 665 | Ala | Tyr | Arg | Ala | Tyr 670 | Gln | Asn |

| TGG | GTC | AAG | AAG | AAT | GGG | GCT | GAG | CAG | ACA | CTG | CCC | ACC | CTG | GGT | CTC | 2181 |
|---|---|---|---|---|---|---|---|---|---|---|---|---|---|---|---|---|

```
        Trp  Val  Lys  Lys  Asn  Gly  Ala  Glu  Gln  Thr  Leu  Pro  Thr  Leu  Gly  Leu
                  675                 680                      685

ACC  AAC  AAC  CAG  CTC  TTC  TTC  CTG  AGT  TTT  GGA  CAG  GTC  TGG  TGT  TCC       2229
Thr  Asn  Asn  Gln  Leu  Phe  Phe  Leu  Ser  Phe  Gly  Gln  Val  Trp  Cys  Ser
     690                      695                      700

GTC  CGC  ACC  CCC  GAG  AGT  TCG  CAC  GAA  GGT  CTC  ATC  ACC  GAT  CCC  CAC       2277
Val  Arg  Thr  Pro  Glu  Ser  Ser  His  Glu  Gly  Leu  Ile  Thr  Asp  Pro  His
705                      710                      715                      720

AGC  CCC  TCC  CGC  TTC  CGG  GTC  ATC  GGC  TCC  ATC  TCC  AAC  TCC  AAG  GAG       2325
Ser  Pro  Ser  Arg  Phe  Arg  Val  Ile  Gly  Ser  Ile  Ser  Asn  Ser  Lys  Glu
                    725                      730                      735

TTC  TCG  GAA  CAC  TTC  CAC  TGC  CCG  CCC  GGC  TCA  CCC  ATG  AAC  CCG  CAT       2373
Phe  Ser  Glu  His  Phe  His  Cys  Pro  Pro  Gly  Ser  Pro  Met  Asn  Pro  His
               740                      745                      750

CAC  AAG  TGT  GAA  GTC  TGG  TGAAGGGCCA  GGCACCCAGA  GCCGAGATGG                     2421
His  Lys  Cys  Glu  Val  Trp
               755

AGGGCAAGGC  GGGGGGAGGC  CTGAGAACAC  CCCCCTGGGC  CCACAAGACT  GCCCCCTCCA   2481
TCCGGCGGCC  AGCCCCCTCC  CCCGACGCTG  CAGGGTGGTC  AGCCGGAACC  AAGCCTGTGA   2541
CATGAGCTCT  CACCGTAAGC  TGAGATTTGA  CCCCCTGTGA  AGACCCGCTC  ATCCAGGCA    2601
CACGTGTGTC  AACTCTGATG  GGTGTTGGGG  CGTTAGCCGG  GTTGCCCACC  GGGCCTGGAC   2661
CCTCACCGAC  AAGGGCAGGG  GAGCCCAGCC  CCCTCCGCCC  ACATGCAGCA  CCAGATATAC   2721
CACAAATACC  ACTGTGTCAA  ATGCTTTAAA  GATATATTTT  TGGGGAAACT  ATTTTTAAA    2781
CATAGTGGAA  TACACTGGAA  ACCTTCAGGG  AAATGATGCA  TTTAAAACAC  TTTTTTTTT    2841
ATGGAAAGGA  TCGGTATATT  TATTATGTTC  TGTTTTCTA   AATAACCT                 2889
```

(2) INFORMATION FOR SEQ ID NO:2:

(i) SEQUENCE CHARACTERISTICS:
    (A) LENGTH: 758 amino acids
    (B) TYPE: amino acid
    (D) TOPOLOGY: linear (ii) MOLECULE TYPE: protein (xi) SEQUENCE DESCRIPTION: SEQ ID NO:2:

```
Met  Ser  Pro  Arg  Gly  Gln  Asp  Leu  Leu  Arg  Ser  Pro  Leu  Leu  Leu  Gly
1                   5                    10                      15

Ser  Glu  Ala  Pro  Gly  Leu  Thr  Ser  Ser  Pro  Phe  Arg  Leu  Pro  Pro  Ser
               20                      25                      30

Leu  Gln  Val  Asn  Phe  Arg  Gly  Pro  Arg  Asn  Gly  Gln  Arg  Cys  Trp  Ala
          35                      40                      45

Ala  Arg  Thr  Pro  Val  Glu  Lys  Arg  Leu  Val  Val  Leu  Val  Ala  Leu  Leu
     50                      55                      60

Ala  Ala  Ala  Leu  Val  Ala  Cys  Leu  Ala  Val  Leu  Gly  Ile  Gln  Tyr  Gln
65                       70                      75                      80

Thr  Arg  Thr  Pro  Ser  Val  Cys  Leu  Ser  Glu  Gly  Cys  Ile  Ser  Val  Thr
               85                      90                      95

Ser  Ser  Ile  Leu  Ser  Ser  Met  Asp  Pro  Thr  Val  Asp  Pro  Cys  Gln  Asp
               100                     105                     110

Phe  Phe  Thr  Tyr  Ala  Cys  Gly  Gly  Trp  Ile  Lys  Ala  Asn  Pro  Val  Pro
               115                     120                     125

Asp  Gly  His  Ser  Arg  Trp  Gly  Thr  Phe  Ser  Asn  Leu  Trp  Glu  His  Asn
     130                     135                     140

Gln  Ala  Ile  Ile  Lys  His  Leu  Leu  Glu  Asn  Ser  Thr  Ala  Ser  Val  Ser
145                     150                     155                     160
```

| | | | | | | | | | | | | | |
|---|---|---|---|---|---|---|---|---|---|---|---|---|---|
| Glu | Ala | Glu | Arg | Lys 165 | Ala | Gln | Val | Tyr 170 | Tyr | Arg | Ala | Cys | Met | Asn 175 | Glu |
| Thr | Arg | Ile | Glu 180 | Glu | Leu | Lys | Ala | Lys 185 | Pro | Leu | Met | Glu | Leu 190 | Ile | Glu |
| Lys | Leu | Gly 195 | Gly | Trp | Asn | Ile | Thr 200 | Gly | Pro | Trp | Asp | Lys 205 | Asp | Asn | Phe |
| Gln | Asp 210 | Thr | Leu | Gln | Val | Val 215 | Thr | Ser | His | Tyr | His 220 | Thr | Ser | Pro | Phe |
| Phe 225 | Ser | Val | Tyr | Val | Ser 230 | Ala | Asp | Ser | Lys | Asn 235 | Ser | Asn | Ser | Asn | Val 240 |
| Ile | Gln | Val | Asp | Gln 245 | Ser | Gly | Leu | Gly | Leu 250 | Pro | Ser | Arg | Asp | Tyr 255 | Tyr |
| Leu | Asn | Lys | Thr 260 | Glu | Asn | Glu | Lys | Val 265 | Leu | Thr | Gly | Tyr | Leu 270 | Asn | Tyr |
| Met | Val | Gln 275 | Leu | Gly | Lys | Leu | Leu 280 | Gly | Gly | Gly | Ala | Glu 285 | Asp | Thr | Ile |
| Arg | Pro 290 | Gln | Met | Gln | Gln | Ile 295 | Leu | Asp | Phe | Glu | Thr 300 | Ala | Leu | Ala | Asn |
| Ile 305 | Thr | Ile | Pro | Gln | Glu 310 | Lys | Arg | Arg | Asp | Glu 315 | Glu | Leu | Ile | Tyr | His 320 |
| Lys | Val | Thr | Ala | Ala 325 | Glu | Leu | Gln | Thr | Leu 330 | Ala | Pro | Ala | Ile | Asn 335 | Trp |
| Leu | Pro | Phe | Leu 340 | Asn | Thr | Ile | Phe | Tyr 345 | Pro | Val | Glu | Ile | Asn 350 | Glu | Ser |
| Glu | Pro | Ile 355 | Val | Ile | Tyr | Asp | Lys 360 | Glu | Tyr | Leu | Ser | Lys 365 | Val | Ser | Thr |
| Leu | Ile | Asn | Ser 370 | Thr | Asp | Lys | Cys 375 | Leu | Leu | Asn | Asn | Tyr 380 | Met | Ile | Trp |
| Asn 385 | Leu | Val | Arg | Lys | Thr 390 | Ser | Ser | Phe | Leu | Asp 395 | Gln | Arg | Phe | Gln | Asp 400 |
| Ala | Asp | Glu | Lys | Phe 405 | Met | Glu | Val | Met | Tyr 410 | Gly | Thr | Lys | Lys 415 | Thr | Cys |
| Leu | Pro | Arg | Trp 420 | Lys | Phe | Cys | Val | Ser 425 | Asp | Thr | Glu | Asn | Thr 430 | Leu | Gly |
| Phe | Ala | Leu 435 | Gly | Pro | Met | Phe | Val 440 | Lys | Ala | Thr | Phe | Ala 445 | Glu | Asp | Ser |
| Lys | Asn 450 | Ile | Ala | Ser | Glu | Ile 455 | Ile | Leu | Glu | Ile | Lys 460 | Lys | Ala | Phe | Glu |
| Glu 465 | Ser | Leu | Ser | Thr | Leu 470 | Lys | Trp | Met | Asp | Glu 475 | Asp | Thr | Arg | Lys | Ser 480 |
| Ala | Lys | Glu | Lys | Ala 485 | Asp | Ala | Ile | Tyr | Asn 490 | Met | Ile | Gly | Tyr | Pro 495 | Asn |
| Phe | Ile | Met | Asp 500 | Pro | Lys | Glu | Leu | Asp 505 | Lys | Val | Phe | Asn | Asp 510 | Tyr | Thr |
| Ala | Val | Pro 515 | Asp | Leu | Tyr | Phe | Glu 520 | Asn | Ala | Met | Arg | Phe 525 | Phe | Asn | Phe |
| Ser | Trp 530 | Arg | Val | Thr | Ala | Asp 535 | Gln | Leu | Arg | Lys | Ala 540 | Pro | Asn | Arg | Asp |
| Gln 545 | Trp | Ser | Met | Thr | Pro 550 | Pro | Met | Val | Asn | Ala 555 | Tyr | Tyr | Ser | Pro | Thr 560 |
| Lys | Asn | Glu | Ile | Val 565 | Phe | Pro | Ala | Gly | Ile 570 | Leu | Gln | Ala | Pro | Phe 575 | Tyr |
| Thr | Arg | Ser | Ser | Pro | Asn | Ala | Leu | Asn | Phe | Gly | Gly | Ile | Gly | Val | Val |

|     |     |     |     |     |     |     | 580 |     |     |     |     |     | 585 |     |     |     |     |     | 590 |     |
|-----|-----|-----|-----|-----|-----|-----|-----|-----|-----|-----|-----|-----|-----|-----|-----|-----|-----|-----|-----|-----|

Val Gly His Glu Leu Thr His Ala Phe Asp Asp Gln Gly Arg Glu Tyr
        595              600                 605

Asp Lys Asp Gly Asn Leu Arg Pro Trp Trp Lys Asn Ser Ser Val Glu
    610              615                 620

Ala Phe Lys Gln Gln Thr Ala Cys Met Val Glu Gln Tyr Gly Asn Tyr
625              630              635                         640

Ser Val Asn Gly Glu Pro Val Asn Gly Arg His Thr Leu Gly Glu Asn
            645                 650                     655

Ile Ala Asp Asn Gly Gly Leu Lys Ala Ala Tyr Arg Ala Tyr Gln Asn
            660              665              670

Trp Val Lys Lys Asn Gly Ala Glu Gln Thr Leu Pro Thr Leu Gly Leu
        675              680              685

Thr Asn Asn Gln Leu Phe Phe Leu Ser Phe Gly Gln Val Trp Cys Ser
    690              695              700

Val Arg Thr Pro Glu Ser Ser His Glu Gly Leu Ile Thr Asp Pro His
705              710              715                         720

Ser Pro Ser Arg Phe Arg Val Ile Gly Ser Ile Ser Asn Ser Lys Glu
            725              730              735

Phe Ser Glu His Phe His Cys Pro Pro Gly Ser Pro Met Asn Pro His
            740              745              750

His Lys Cys Glu Val Trp
            755

( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: modified_base
        ( B ) LOCATION: 51..52
        ( D ) OTHER INFORMATION: /mod_base=OTHER
          / note="N =A, G, C or T"

( x i ) SEQUENCE DESCRIPTION: SEQ ID NO:3:

TCCGTGCGAC TGTAGTTCTG TGTGGCACCA TTGTAACTGA AATAAAGTAC TNATACCGAT 60

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: modified_base
        ( B ) LOCATION: 12..21
        ( D ) OTHER INFORMATION: /mod_base=OTHER
          / note="N =A, G, C or T"

( x i ) SEQUENCE DESCRIPTION: SEQ ID NO:4:

GAGAAGCTTC CNGARATHGT NTTYCC 26

( 2 ) INFORMATION FOR SEQ ID NO:5:

```
        ( i ) SEQUENCE CHARACTERISTICS:
              ( A ) LENGTH: 26 base pairs
              ( B ) TYPE: nucleic acid
              ( C ) STRANDEDNESS: single
              ( D ) TOPOLOGY: linear ( i i ) MOLECULE TYPE: DNA ( i x ) FEATURE:
              ( A ) NAME/KEY: modified_base
              ( B ) LOCATION: 12..24
              ( D ) OTHER INFORMATION: /mod_base=OTHER
                    / note="N =A, G, C or T"

( x i ) SEQUENCE DESCRIPTION: SEQ ID NO:5:

GAGATCGATA ARTTYAANGC RTTNGG                                              2 6
```